United States Patent
Miesak

(10) Patent No.: US 9,897,544 B2
(45) Date of Patent: Feb. 20, 2018

(54) LATENT FINGERPRINT DETECTION

(71) Applicant: LOCKHEED MARTIN CORPORATION, Bethesda, MD (US)

(72) Inventor: Edward J. Miesak, Windermere, FL (US)

(73) Assignee: LOCKHEED MARTIN CORPORATION, Bethesda, MD (US)

(*) Notice: Subject to any disclaimer, the term of this patent is extended or adjusted under 35 U.S.C. 154(b) by 241 days.

(21) Appl. No.: 14/675,813

(22) Filed: Apr. 1, 2015

(65) Prior Publication Data

US 2015/0215509 A1    Jul. 30, 2015

Related U.S. Application Data

(63) Continuation of application No. 14/423,582, filed as application No. PCT/US2012/052115 on Aug. 23, 2012, now abandoned.
(Continued)

(51) Int. Cl.
| | |
|---|---|
| G01N 21/00 | (2006.01) |
| G01N 21/64 | (2006.01) |
| A61B 5/1172 | (2016.01) |
| G06K 9/00 | (2006.01) |
| G06K 9/20 | (2006.01) |
| H04N 5/225 | (2006.01) |

(Continued)

(52) U.S. Cl.
CPC ........ *G01N 21/6447* (2013.01); *A61B 5/1172* (2013.01); *G01N 21/31* (2013.01);
(Continued)

(58) Field of Classification Search
CPC ............ G01N 21/6447; G01N 21/6428; A61B 5/117; G01J 3/4406; G06K 9/00013
See application file for complete search history.

(56) References Cited

U.S. PATENT DOCUMENTS

| | | | |
|---|---|---|---|
| 4,120,585 A | 10/1978 | DePalma et al. | |
| 4,176,205 A * | 11/1979 | Molina | A61B 5/1172 156/241 |

(Continued)

FOREIGN PATENT DOCUMENTS

| | | |
|---|---|---|
| CN | 2603449 | 2/2004 |
| CN | 201210214 | 3/2009 |

(Continued)

OTHER PUBLICATIONS

James Robertson, 2004 by CRC Press LLC, "The Practice of Crime Scene Investigation" (pp. 1-424).
(Continued)

*Primary Examiner* — Kara E Geisel
*Assistant Examiner* — Maurice Smith
(74) *Attorney, Agent, or Firm* — Oblon, McClelland, Maier & Neustadt, L.L.P.

(57) ABSTRACT

Systems, devices, and methods for detecting a contaminant on a substrate are discussed herein. Variations of such systems, devices, and methods may include one or more illumination sources that emit illumination at one or more desired wavelength ranges to illuminate one or more areas on the substrate; where the desired wavelength range is one that is absorbed by the contaminant while causing the substrate to fluoresce. Such fluorescence may be detected with a visible-spectrum detector, which will also detect the contaminant as a darker contrast area against the fluorescence. In some variations, an illumination source includes a broad-spectrum light source and a waveband filtering device that filters all but the desired illumination waveband out of the broad-spectrum light generated by the broad-spectrum light source.

16 Claims, 24 Drawing Sheets

Related U.S. Application Data

(60) Provisional application No. 61/573,077, filed on Aug. 26, 2011, provisional application No. 61/530,306, filed on Sep. 1, 2011, provisional application No. 61/538,020, filed on Sep. 22, 2011, provisional application No. 61/602,950, filed on Feb. 24, 2012, provisional application No. 61/602,956, filed on Feb. 24, 2012, provisional application No. 61/606,886, filed on Mar. 5, 2012, provisional application No. 61/606,898, filed on Mar. 5, 2012.

(51) Int. Cl.
*H04N 5/33* (2006.01)
*G01N 21/31* (2006.01)
*A61B 5/00* (2006.01)

(52) U.S. Cl.
CPC ....... *G06K 9/00013* (2013.01); *G06K 9/2018* (2013.01); *H04N 5/2254* (2013.01); *H04N 5/2256* (2013.01); *H04N 5/33* (2013.01); *A61B 5/0071* (2013.01); *G06K 2009/00946* (2013.01)

(56) References Cited

U.S. PATENT DOCUMENTS

| | | |
|---|---|---|
| 4,247,784 A | 1/1981 | Henry |
| 4,351,588 A | 9/1982 | Zullig |
| 4,632,807 A | 12/1986 | Marsoner |
| 4,783,167 A | 11/1988 | Schiller et al. |
| 4,785,171 A | 11/1988 | Dowling, Jr. et al. |
| 4,794,260 A * | 12/1988 | Asano ............ A61B 5/1172 250/458.1 |
| 4,989,968 A | 2/1991 | Freedman |
| 5,004,349 A | 4/1991 | Sato et al. |
| 5,099,131 A | 3/1992 | Brownrigg et al. |
| 5,109,427 A | 4/1992 | Yang |
| 5,123,723 A | 6/1992 | Chesnutt et al. |
| 5,210,588 A | 5/1993 | Lee |
| 5,233,404 A | 8/1993 | Lougheed et al. |
| 5,266,805 A | 11/1993 | Edgar |
| 5,313,265 A | 5/1994 | Hayes et al. |
| 5,629,764 A | 5/1997 | Bahuguna et al. |
| 5,720,772 A | 2/1998 | Eckhouse |
| 5,812,252 A | 9/1998 | Bowker et al. |
| 5,912,768 A | 6/1999 | Sissom et al. |
| 5,963,657 A | 10/1999 | Bowker et al. |
| 6,005,963 A | 12/1999 | Bolle et al. |
| 6,115,484 A | 9/2000 | Bowker et al. |
| 6,124,238 A | 9/2000 | Chapman et al. |
| 6,127,189 A | 10/2000 | Joullie et al. |
| 6,144,453 A | 11/2000 | Hallerman et al. |
| 6,193,425 B1 | 2/2001 | Edgar |
| 6,292,576 B1 | 9/2001 | Brownlee |
| 6,354,724 B1 | 3/2002 | Sakashita |
| 6,485,981 B1 * | 11/2002 | Fernandez ............ G01N 33/92 436/164 |
| 6,488,892 B1 | 12/2002 | Burton et al. |
| 6,503,695 B1 | 1/2003 | Miyazawa et al. |
| 6,558,052 B2 | 5/2003 | Edgar |
| 6,643,390 B1 | 11/2003 | Clark et al. |
| 6,665,427 B1 | 12/2003 | Keagy |
| 6,668,071 B1 | 12/2003 | Minkin et al. |
| 6,885,017 B2 | 4/2005 | Lee et al. |
| 6,989,547 B2 | 1/2006 | Lee et al. |
| 6,995,384 B2 | 2/2006 | Lee et al. |
| 7,039,224 B2 | 5/2006 | Hamid et al. |
| 7,181,052 B2 | 2/2007 | Fujieda |
| 7,212,330 B2 | 5/2007 | Seo et al. |
| 7,234,641 B2 | 6/2007 | Olmstead |
| 7,295,688 B2 | 11/2007 | Hara et al. |
| 7,310,153 B2 * | 12/2007 | Kiesel ............ G01J 9/0246 356/454 |
| 7,346,200 B1 | 3/2008 | Tsipouras et al. |
| 7,420,663 B2 | 9/2008 | Wang et al. |
| 7,489,391 B2 | 2/2009 | Engheta et al. |
| 7,787,110 B2 | 8/2010 | Raguin et al. |
| 7,846,191 B2 | 12/2010 | Vaynberg et al. |
| 8,077,929 B2 | 12/2011 | Heidt |
| 8,180,120 B2 | 5/2012 | Hook |
| 8,371,695 B2 | 2/2013 | Papac et al. |
| 8,396,319 B2 | 3/2013 | Pugh, Jr. et al. |
| 8,437,517 B2 | 5/2013 | Miesak et al. |
| 8,805,033 B2 | 8/2014 | Miesak et al. |
| 9,188,546 B2 | 11/2015 | Miesak et al. |
| 2002/0190212 A1 | 12/2002 | Boas et al. |
| 2003/0118219 A1 | 6/2003 | Higuchi et al. |
| 2003/0156284 A1 | 8/2003 | Farr |
| 2003/0156740 A1 | 8/2003 | Siegel et al. |
| 2003/0185425 A1 | 10/2003 | Nishikawa |
| 2004/0026635 A1 | 2/2004 | Lee et al. |
| 2005/0141756 A1 | 6/2005 | Lee et al. |
| 2006/0008129 A1 | 1/2006 | Lee et al. |
| 2006/0120573 A1 | 6/2006 | Iori |
| 2006/0126168 A1 * | 6/2006 | Treado ............ G01J 3/32 359/385 |
| 2007/0177233 A1 | 8/2007 | Ichikawa et al. |
| 2007/0201733 A1 | 8/2007 | Hara |
| 2008/0198379 A1 * | 8/2008 | Coker ............ G01N 21/645 356/317 |
| 2008/0204710 A1 * | 8/2008 | Harrison ............ G01J 3/02 356/51 |
| 2009/0052752 A1 | 2/2009 | Monden |
| 2009/0155456 A1 | 6/2009 | Benkley et al. |
| 2010/0303311 A1 | 12/2010 | Shin et al. |
| 2010/0311005 A1 | 12/2010 | Liang |
| 2011/0076383 A1 | 3/2011 | Reedy et al. |
| 2011/0121758 A1 | 5/2011 | Bierhuizen et al. |
| 2012/0105586 A1 | 5/2012 | Miesak et al. |
| 2012/0138728 A1 | 6/2012 | Brunton et al. |
| 2013/0301887 A1 | 11/2013 | Miesak et al. |
| 2014/0254894 A1 | 9/2014 | Miesak et al. |
| 2015/0317505 A1 | 11/2015 | Miesak et al. |
| 2015/0338745 A1 | 11/2015 | Fukazawa |
| 2016/0026845 A1 | 1/2016 | Miesak et al. |

FOREIGN PATENT DOCUMENTS

| | | |
|---|---|---|
| JP | H05-220131 | 8/1993 |
| JP | H06-147852 | 5/1994 |
| JP | 2001-034738 | 9/2001 |
| WO | 2006073450 | 7/2006 |
| WO | 2010/064034 | 6/2010 |
| WO | 2010071215 | 6/2010 |

OTHER PUBLICATIONS

Bartick et al., 2002, "Spectrochemical Analysis and Hyperspectral Imaging of latent Fingerprints" (pp. 61-64).
Austin Richards, Mar. 28, 2010, "Reflected Ultraviolet Imaging for Forensics Applications" (pp. 1-31).
Tahtouh et al., 2005, "The Detection and Enhancement of Latent Fingermaks Using Infrared Chemical Imaging" (pp. 1-9).
"Forensic Lab 8.0: Revealing Latent Fingerprints—Introduction", Aug. 16, 2009, pp. 1-17.
Seto, Eileen K. et al. "Imaging Electrophoretic Gels with a Scanning Beam Laser Macroscope," Electrophoresis, Wiley Interscience, DE, Apr. 15, 2005, pp. 934-940, vol. 16.
"Chapter 2: Finger Mark Examination Techniques within Scope of ISO 17025 2.1 Visual Examination," Mar. 26, 2013, pp. 291-293, XP055130668.
Lin et al., "Polarization and Specular-Reflection-Based, Non-contact Latent Fingerprint Imaging and Lifting", 2006, Journal of the Optical Society of America A, vol. 23, Issue 9, pp. 2137-2153.

* cited by examiner

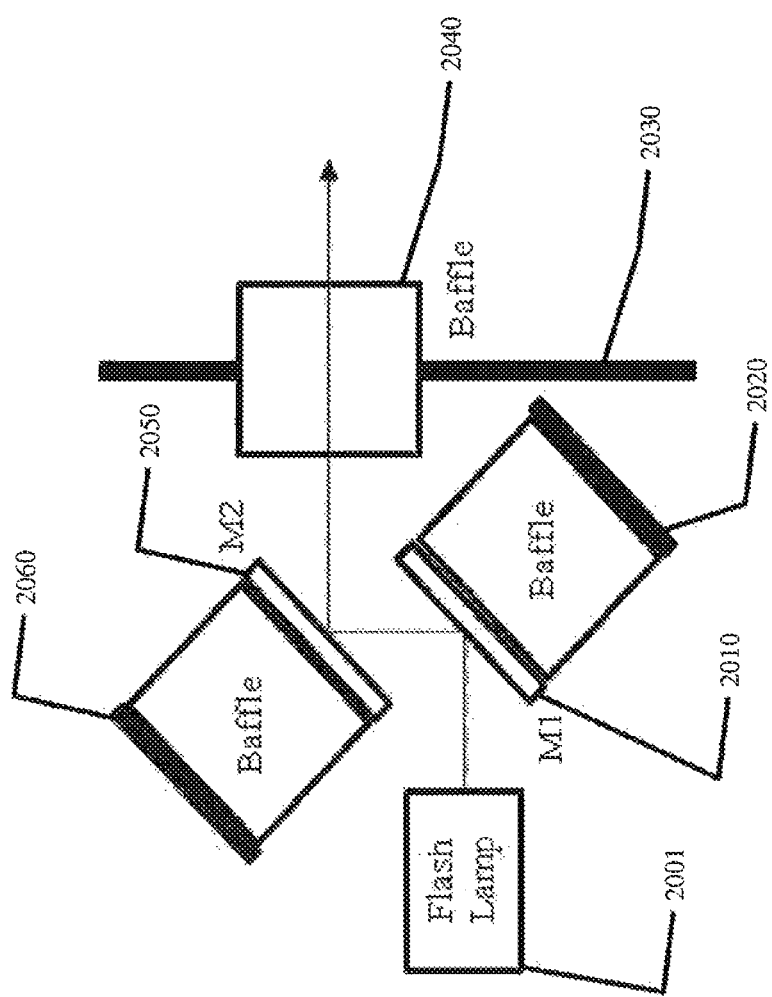

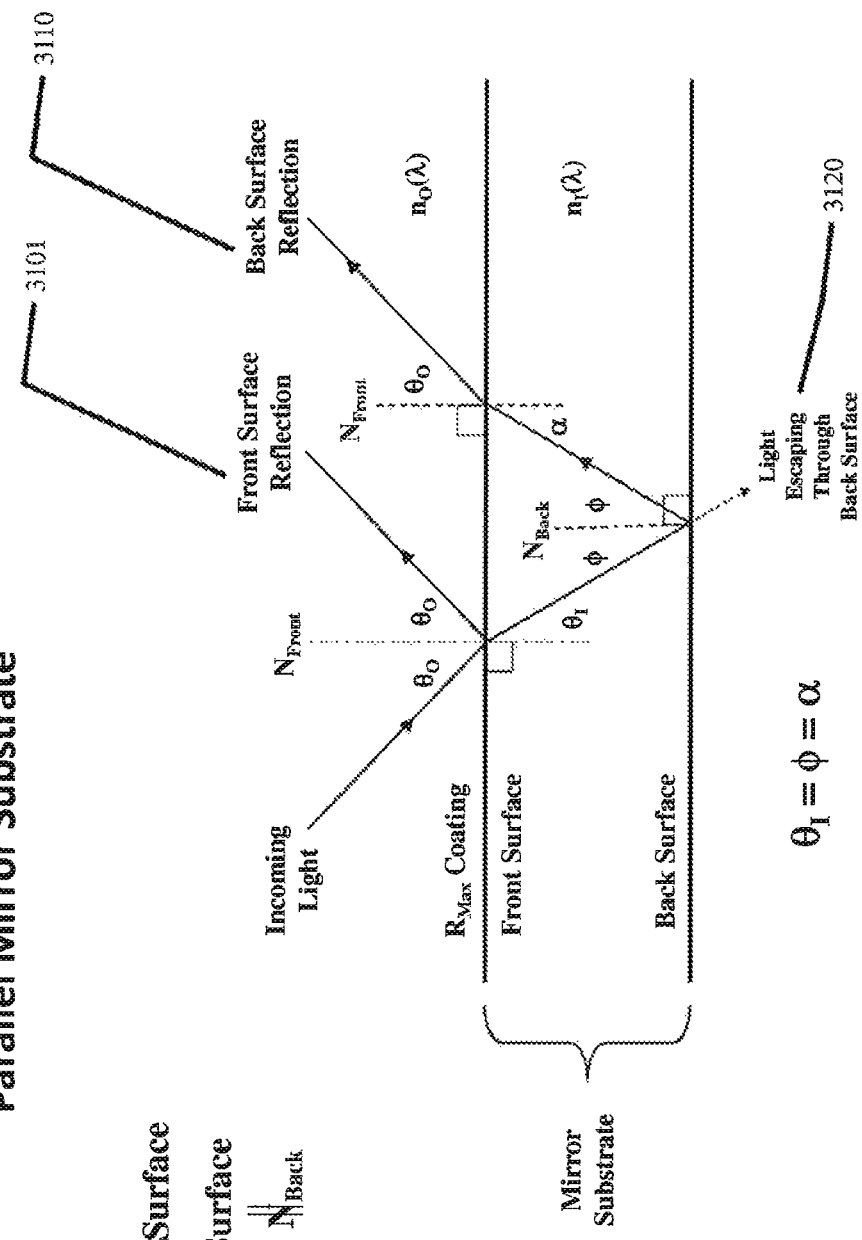

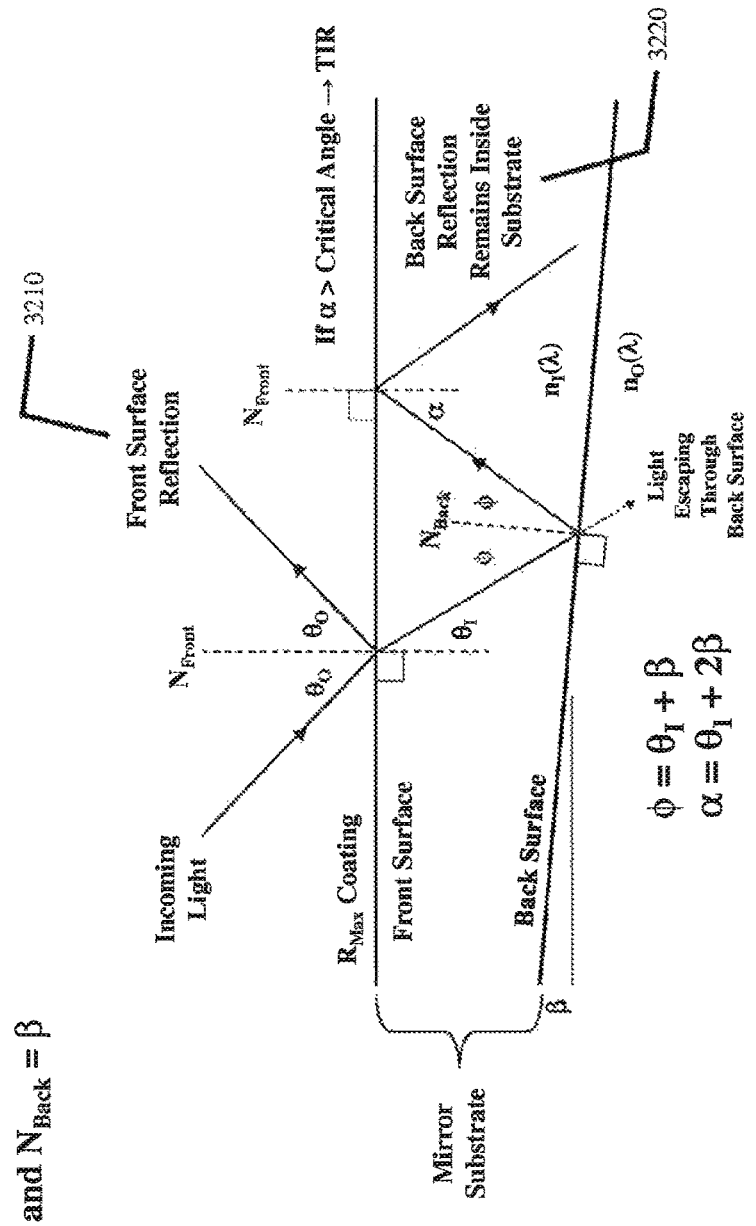

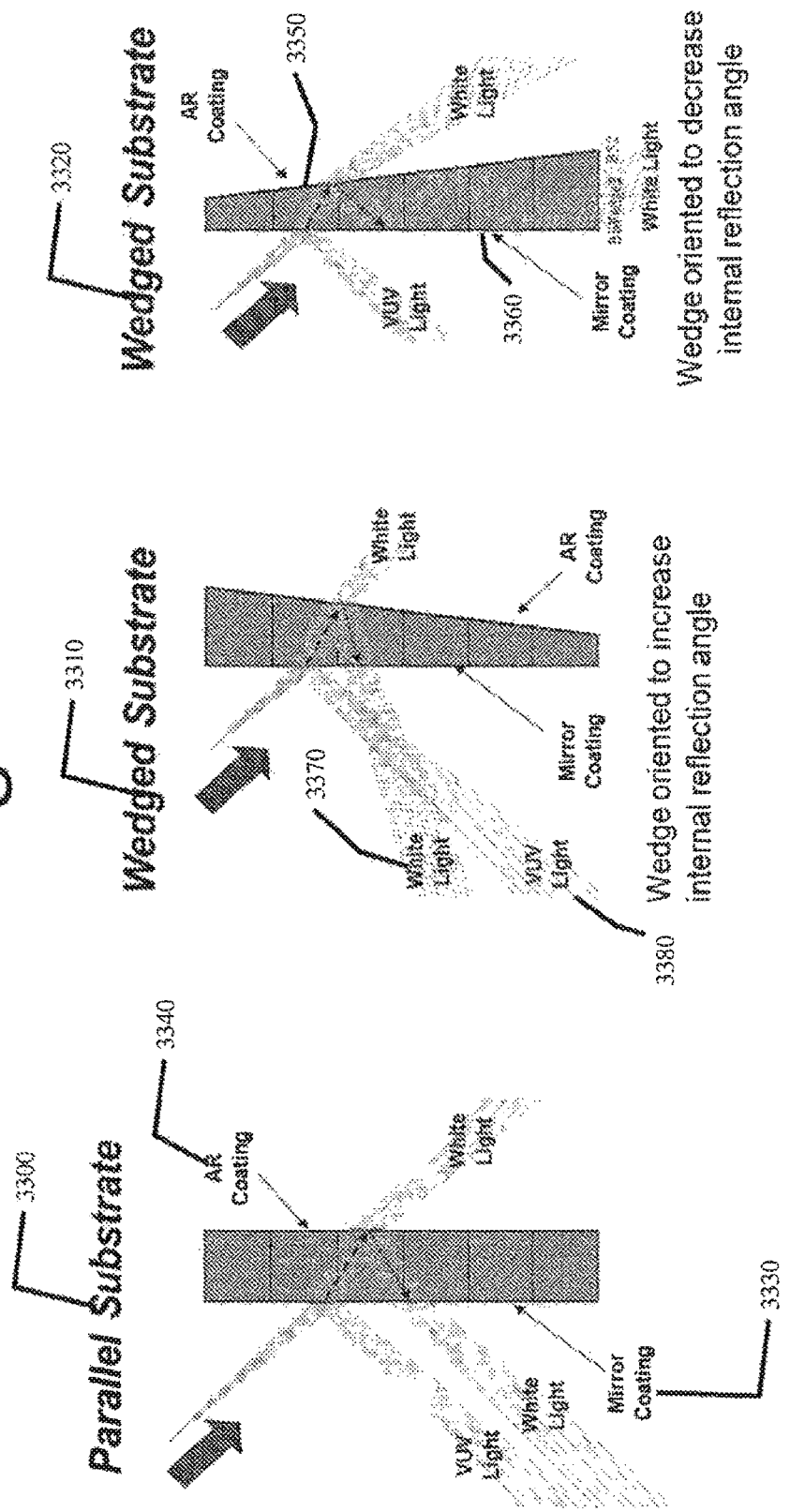

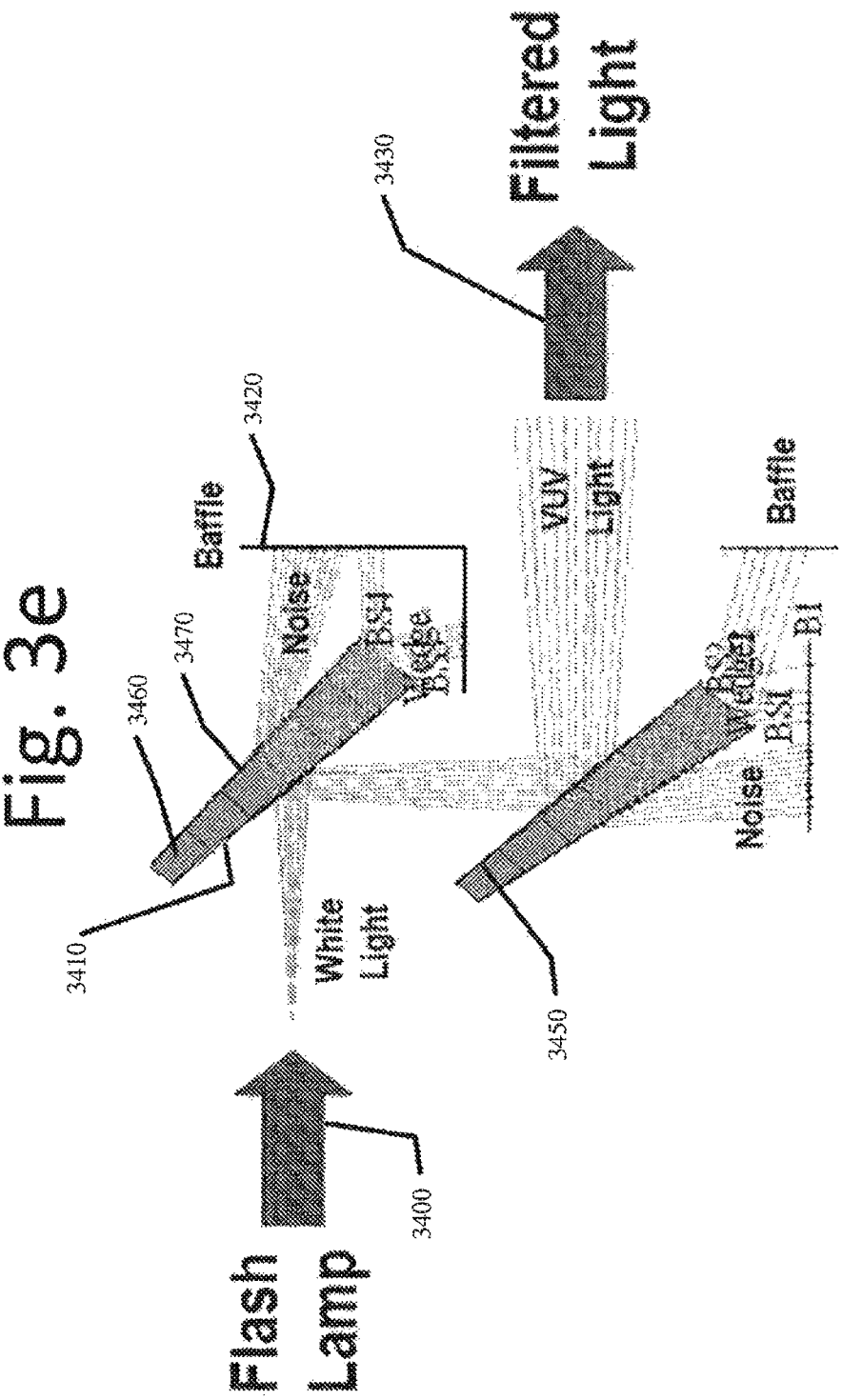

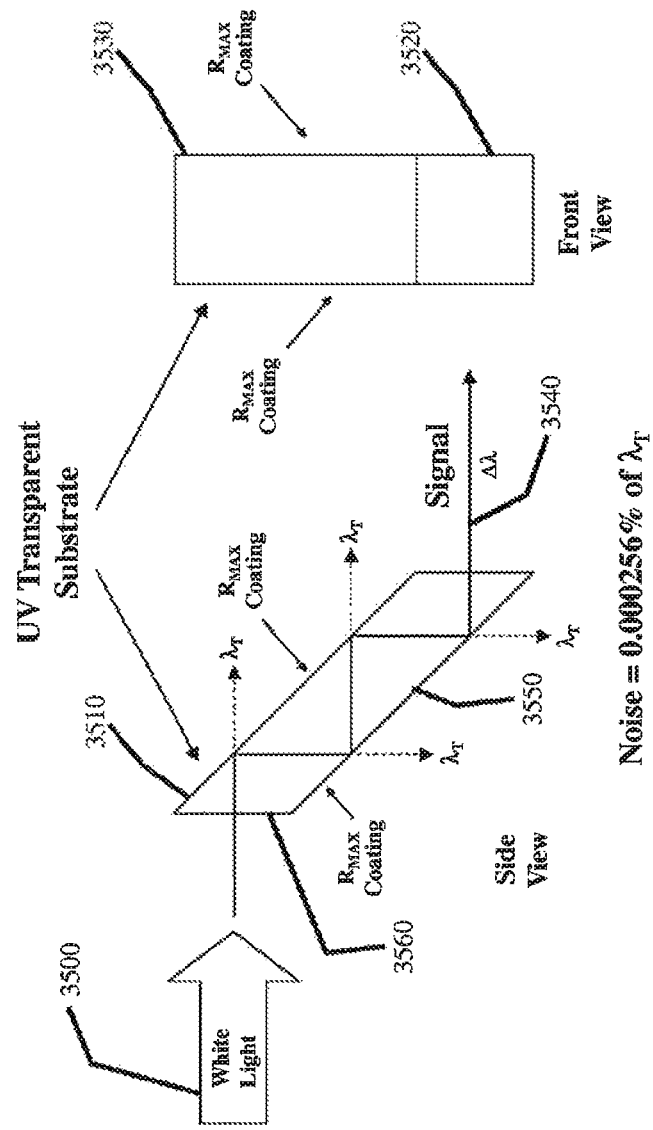

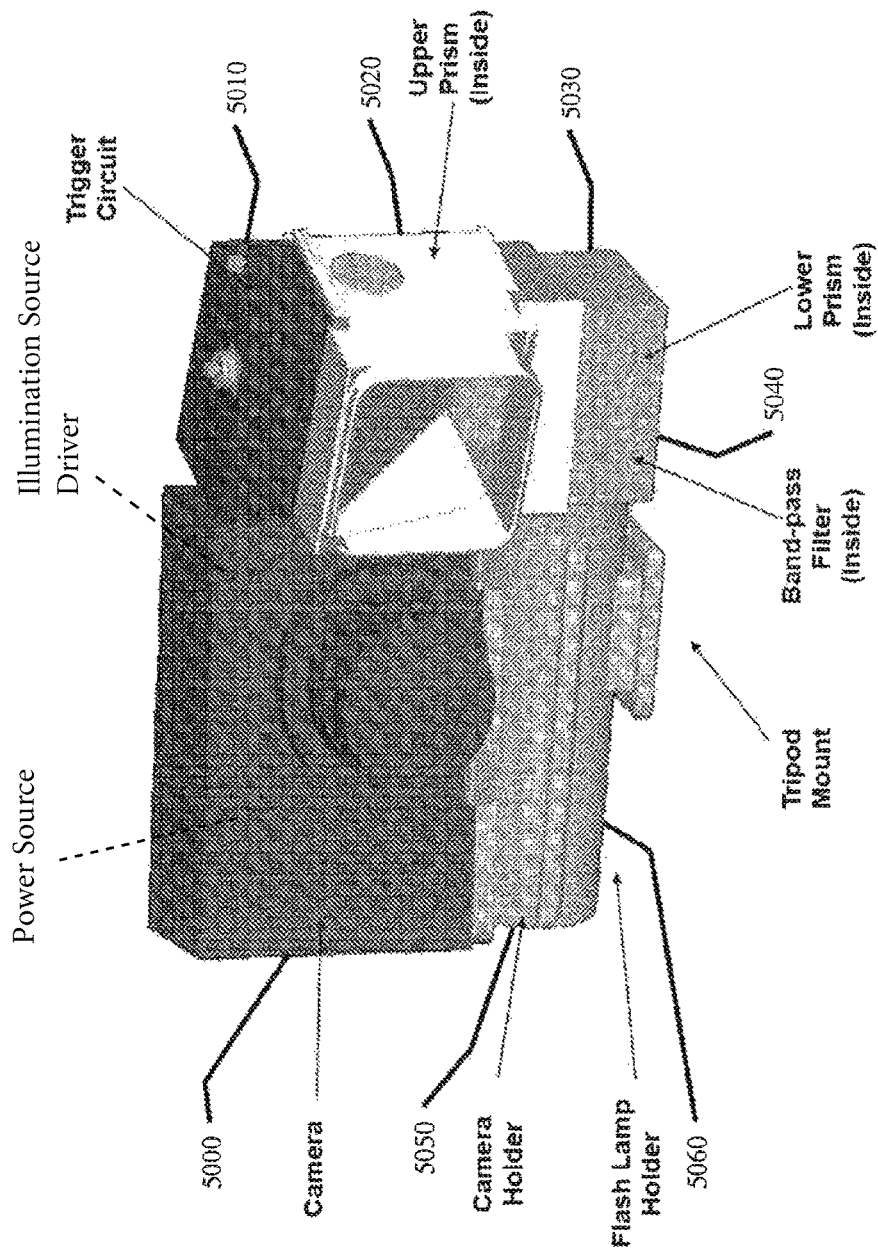

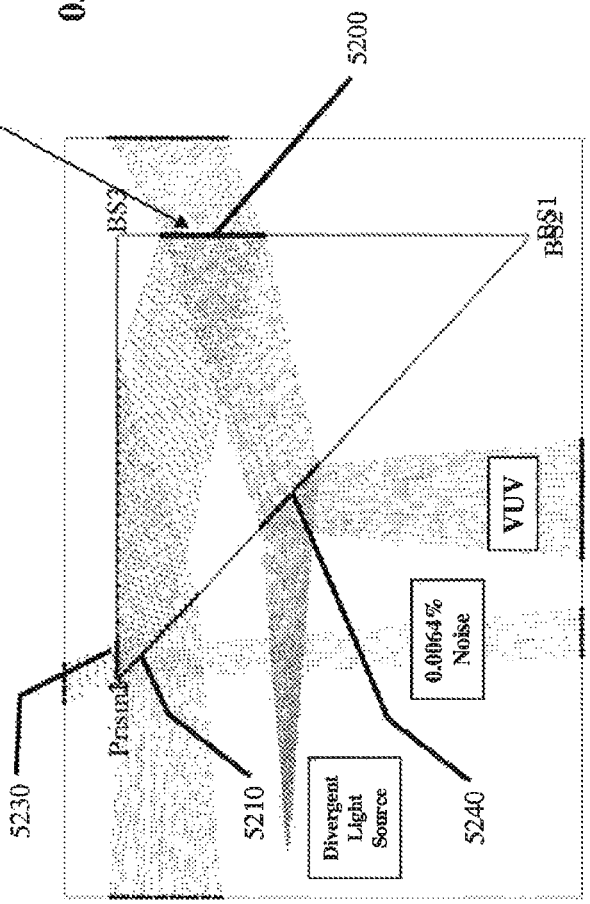

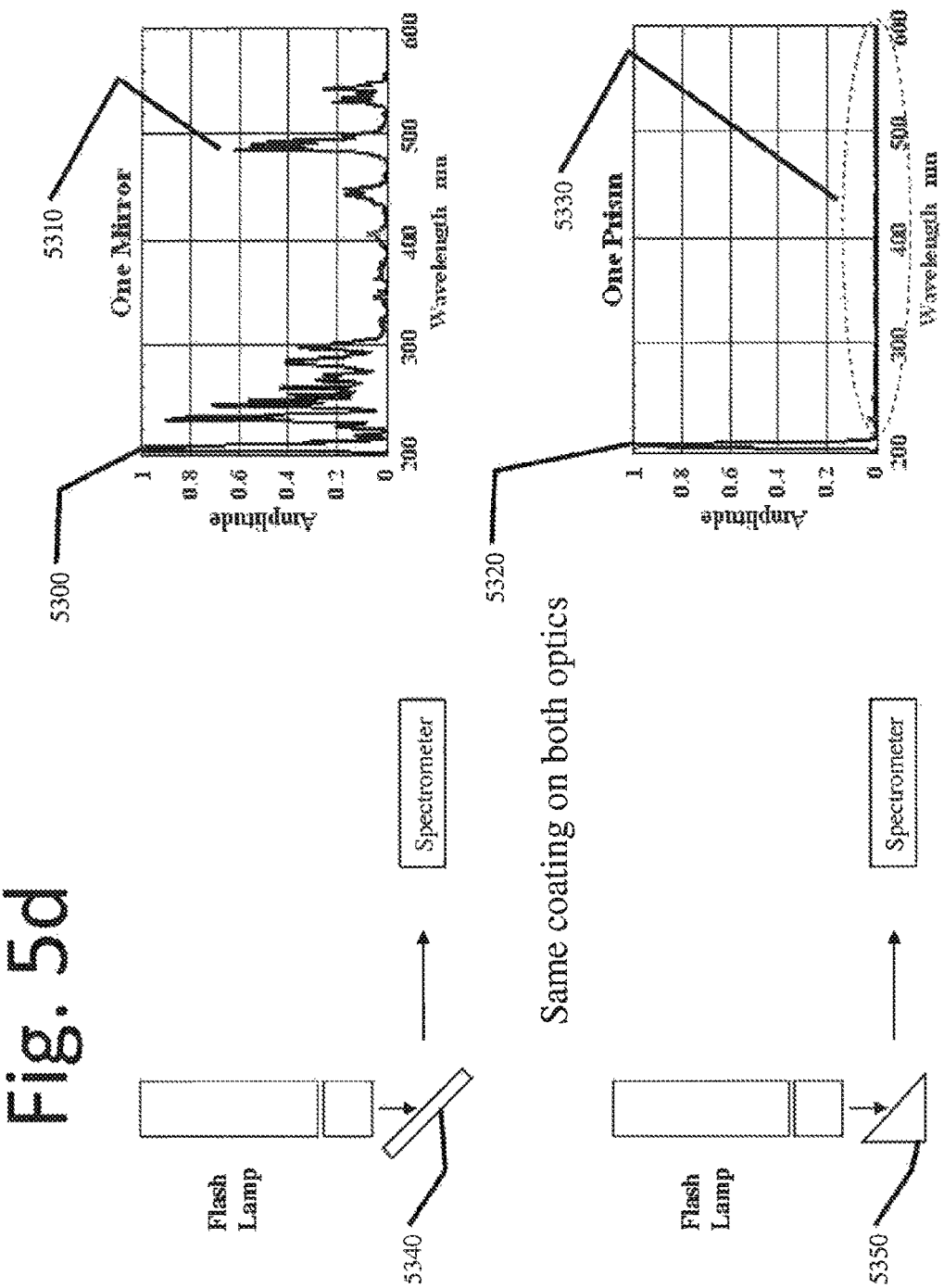

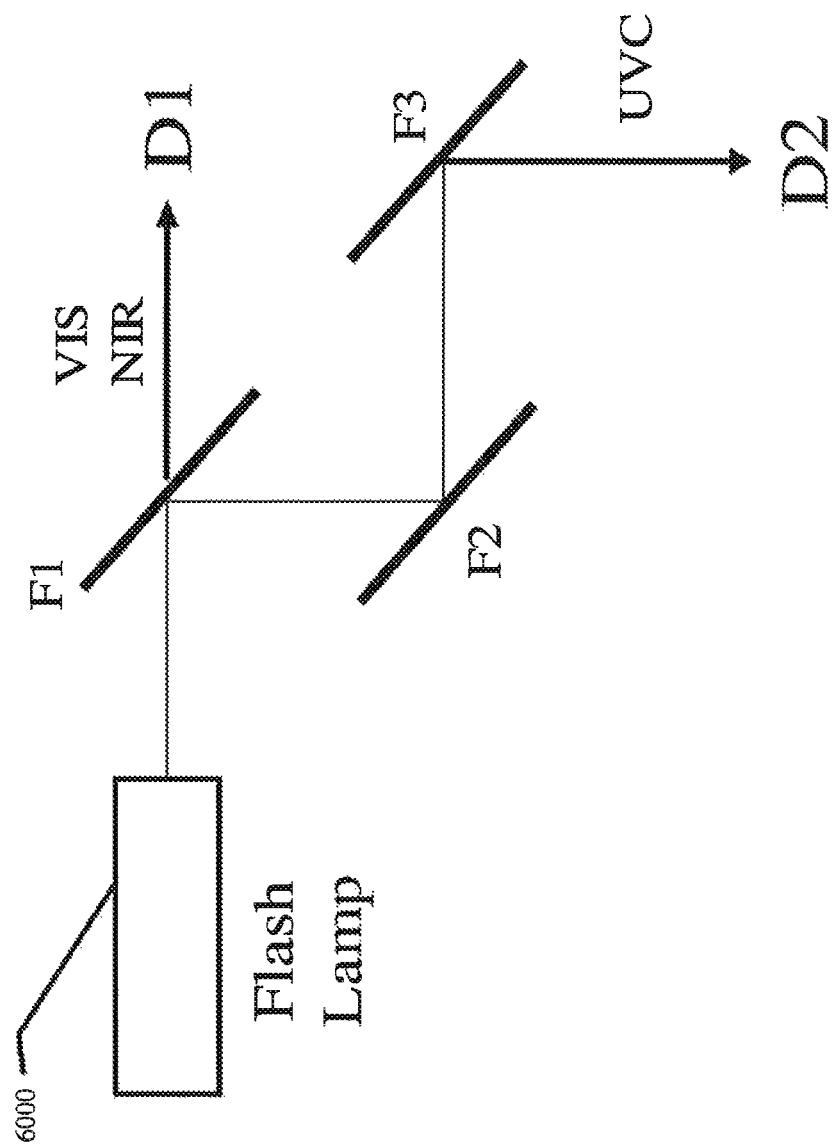

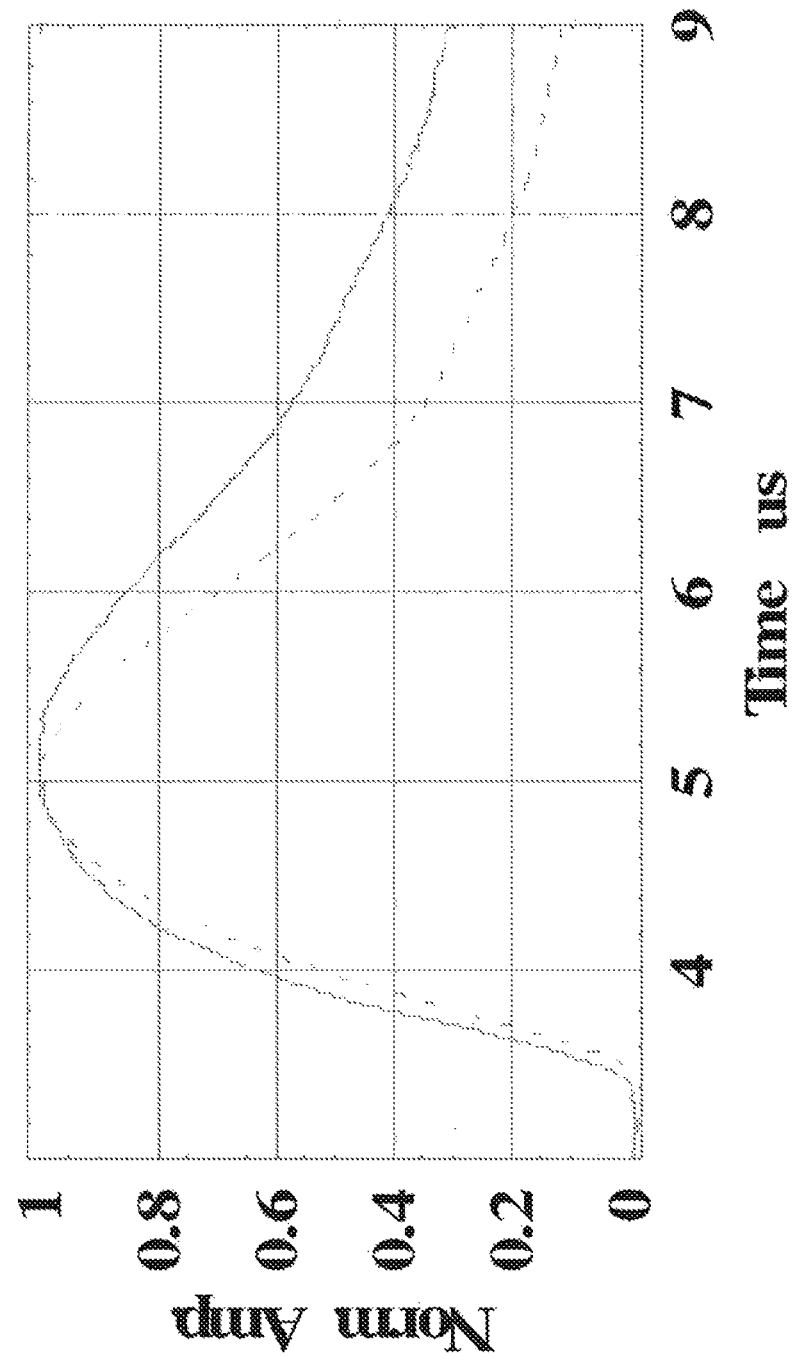

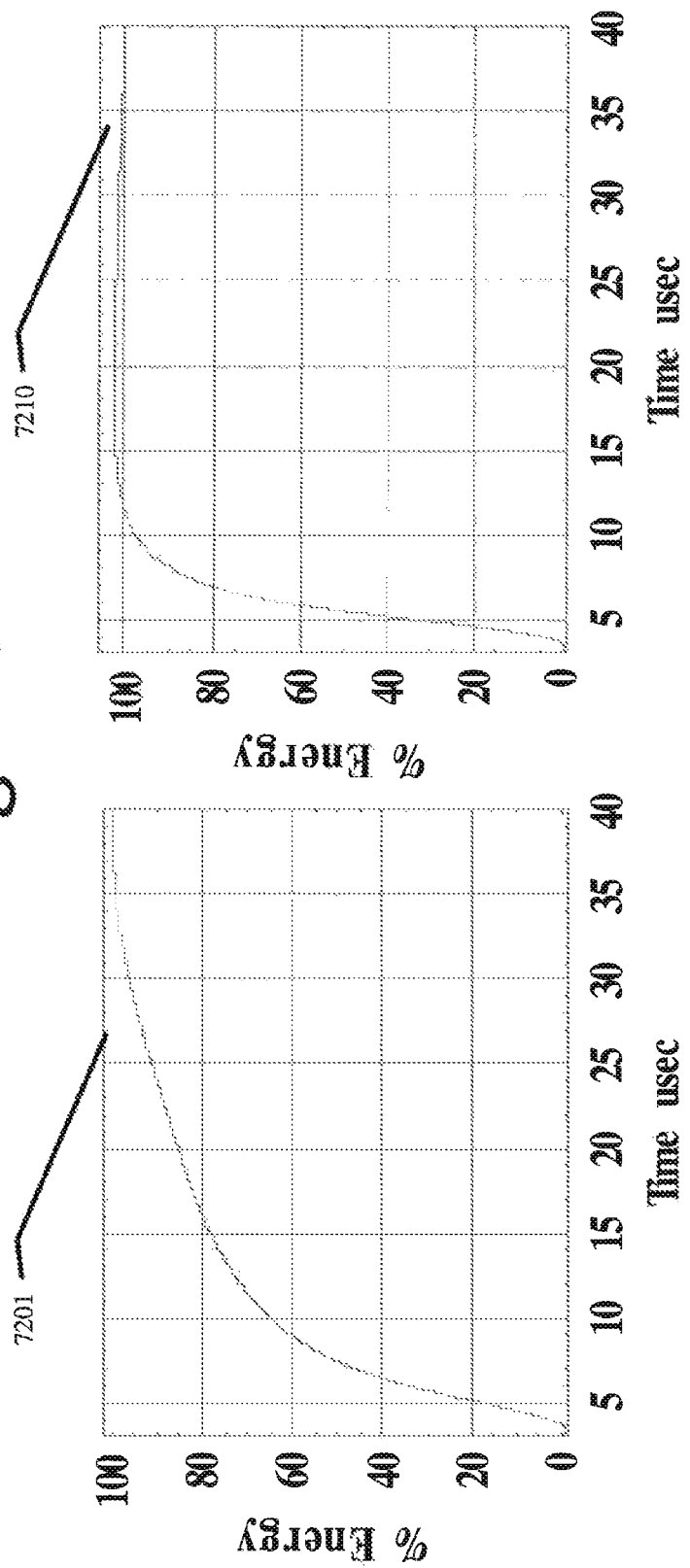

LATENT FINGERPRINT DETECTION

CROSS-REFERENCE TO RELATED APPLICATIONS

This application is a Continuation of U.S. application Ser. No. 14/423,582 filed Feb. 24, 2015, which is a 371 national stage of PCT/US2012/052115 filed Aug. 23, 2012, which claims the benefit of U.S. Provisional Application Nos. 61/573,077 filed Aug. 26, 2011; 61/530,306 filed Sep. 1, 2011; 61/538,020 filed Sep. 22, 2011; 61/602,950 filed Feb. 24, 2012; 61/602,956 filed Feb. 24, 2012; 61/606,886 filed Mar. 5, 2012; and 61/606,898 filed. Mar. 5, 2012, the entire contents of all of which are hereby incorporated by reference.

TECHNICAL BACKGROUND

Currently, fingerprint detection technologies are limited to trial-and-error techniques to locate a fingerprint-bearing surface, and yet more trial-and-error techniques to bring the fingerprint into relief against the surface to render it visible/scannable.

Optical detection of latent fingerprints is critically dependent on image contrast. Latent fingerprints are very low contrast objects and therefore using only optical techniques they are difficult to resolve/collect. Lifting latent fingerprints often requires the use of chemical techniques (i.e. processing by ninhydrin) and significant time (3+ days) to lift the fingerprints, which may damage the surface and/or destroy any underlying DNA or material evidence included in the fingerprint (i.e. traces of whatever the person leaving the print may have handled previously)

SUMMARY

Variations of the systems, methods, techniques, devices, and components discussed herein may pertain to a device for detecting a contaminant on a substrate, the device comprising: an illumination source that emits illumination at a desired wavelength range to illuminate an area on the substrate; where the desired wavelength range is one that is absorbed by the contaminant while causing the substrate to fluoresce; and a visible-spectrum imaging device that captures an image of the illuminated contaminant contrasted against the fluorescing substrate; where the illumination source includes a broad-spectrum light source and a waveband filtering device that filters all but the desired illumination waveband out of the broad-spectrum light generated by the broad-spectrum light source.

In some variations, the waveband filtering device includes a first optical element having a waveband-specific dielectric coating on a first reflecting surface such that the optical element reflects only the desired illumination waveband from the first reflecting surface; and the emitted illumination includes light reflected from the first reflecting surface.

In some variations, the first optical element includes a first mirror and where the first reflecting surface is a front surface of the first mirror. In some variations, the first mirror is a wedge-shaped mirror having a wedge angle that creates total internal reflection with respect to any light reflected from a back surface of the mirror. In some variations, the optical element includes a first prism and where the first reflecting surface is a surface of the prism.

In some variations, the waveband filtering device further including a second optical element substantially similar to the first optical element; where the first optical element is configured to filter light from the illumination source; where the second optical element is configured to filter light reflected by the first mirror; and where the emitted illumination includes light reflected by the second mirror.

In some variations, the imaging device is a portable camera, the illumination source is mounted to the imaging device, and the device further comprises: an illumination source driver that drives the illumination source in response to an activation pulse; a power source that provides power to the illumination source driver and the illumination source; and a trigger circuit that controls activation pulse width and activation pulse rate of the illumination source. In some variations, the broad-spectrum light source is a xenon flash lamp.

In some variations, the illumination source includes: a light-proof housing disposed around the broad-spectrum light source and the waveband filtering device; and a first baffle disposed between the broad-spectrum light source and the waveband filtering device, the first baffle being configured to exclude light emitted by the broad spectrum light source but not filtered by the waveband filtering device from the emitted illumination. Further variations may include a second baffle disposed between the waveband filtering device and an illumination output aperture of the light-proof housing; the emitted illumination exiting the light-proof housing through the output aperture; and the second baffle being configured to exclude light scattered inside the Light-proof housing from the emitted illumination.

Some variations may include a negative lens disposed between the broad-spectrum light source and the first baffle, the lens being configured to establish a desired field of view for the emitted illumination.

In some variations, the trigger circuit is configured to provide an activation pulse width that causes the broad-spectrum light source to emit the desired waveband while limiting emission of wavebands which the waveband filtering device is configured to filter out.

In some variations, the contaminant is not treated with any chemicals or contrast agents prior to illumination. In some variations, the contaminant is a latent fingerprint and where the desired illumination waveband is a VUV (vacuum ultra-violet) waveband.

In some variations, the waveband filtering device includes an optical absorption portion that absorbs portions of the broad spectrum illumination not within the desired illumination waveband. In some variations, the optical element is made of filter glass.

Variations of the systems, methods, techniques, devices, and components discussed herein may pertain to a device for detecting a latent fingerprint on a substrate, the device comprising: an illumination source that emits illumination at a VUV (vacuum ultra-violet) wavelength range to illuminate an area on the substrate, where the emitted illumination is absorbed by the fingerprint while causing the substrate to fluoresce; and a visible-spectrum imaging device that captures an image of the illuminated fingerprint contrasted against the fluorescing substrate; where the illumination source includes a broad-spectrum light source and a waveband filtering device that filters all but the VUV illumination waveband out of the broad-spectrum generated by the broad-spectrum light source; the waveband filtering device including a first mirror in optical communication with the broad-spectrum light source and a second mirror in optical communication with the first mirror; the first and second mirrors both being wedge-shaped mirrors, each having a wedge angle that creates total internal reflection with respect to any light reflected from a back surface of the mirror; and the first and second mirrors both being equipped with a VUV dielectric coating on a front reflecting surface such that each mirror reflects only the VUV illumination waveband from its front reflecting surface.

Variations of the systems, methods, techniques, devices, and components discussed herein may pertain to a device for detecting a latent fingerprint on a substrate, the device comprising: an illumination source that emits collimated illumination at a mid-wave or long-wave infra-red illumination to illuminate an area on the substrate, where the emitted illumination is absorbed by the fingerprint at a substantially higher level than by the substrate; and an infra-red imaging device that captures an image of the illuminated fingerprint contrasted against the substrate; where the collimated infra-red beam source is capable of providing illumination to a target more than ten feet away from the illumination source for latent fingerprint detection; and where the imaging device is co-located with the infra-red beam source.

Variations of the systems, methods, techniques, devices, and components discussed herein may pertain to a device for detecting a latent fingerprint on a substrate, the device comprising: an illumination source that emits illumination at a VUV (vacuum ultra-violet) wavelength range to illuminate an area on the substrate, where the emitted illumination is absorbed by the fingerprint while causing the substrate to fluoresce; and a visible-spectrum imaging device that captures an image of the illuminated fingerprint contrasted against the fluorescing substrate; where the illumination source includes a broad-spectrum light source and a waveband filtering device that filters all but the VUV illumination waveband out of the broad-spectrum generated by the broad-spectrum light source; the waveband filtering device including a first optical element in optical communication with the broad-spectrum light source and a second optical element in optical communication with the first optical element; the first and second optical elements both being equipped with a VUV dielectric coating on a reflecting surface such that each optical element reflects only the VUV illumination waveband from the reflecting surface; and the first and second optical elements both being configured to remove light not reflected by the reflecting surface from the output illumination.

In some variations, the latent fingerprint is not treated with any chemicals or contrast agents prior to illumination. In some variations, the first and second optical elements are prisms. In some variations, the device further includes a negative lens disposed between the broad-spectrum light source and the waveband filtering device. In some variations, the optical elements are made of filter glass.

Variations of the systems, methods, techniques, devices, and components discussed herein may pertain to a method of detecting a contaminant on a substrate, the method comprising: emitting illumination at a desired wavelength range to illuminate an area on the substrate; where the desired wavelength range is one that is absorbed by the contaminant while causing the substrate to fluoresce; and capturing a visible-spectrum image of the illuminated contaminant contrasted against the fluorescing substrate; where emitting includes generating broad-spectrum light and filtering all but the desired illumination waveband out of the broad-spectrum light.

In some variations, the step of filtering includes first reflecting the broad-spectrum light with a first optical element having a waveband-specific dielectric coating on a first reflecting surface such that only the desired illumination waveband is reflected from the first reflecting surface.

In some variations, the step of reflecting includes directing light outside of the desired illumination waveband along an optical path other than that followed by the desired illumination waveband such that light outside of the desired illumination waveband is excluded from the emitted illumination.

Some variations include a step of second reflecting the first-reflected light with a second optical element having the waveband-specific dielectric coating. In some variations, the contaminant is a latent fingerprint, the fingerprint is not treated with any chemicals or contrast agents prior said emitting; and the desired illumination waveband is a VUV (vacuum ultra-violet) waveband.

In some variations, the method includes a step of suppressing a portion of the broad-spectrum light before the broad-spectrum light reaches the waveband filtering device such that light emitted by the broad spectrum light source but not filtered by the waveband filtering device is suppressed from the emitted illumination.

In some variations, the broad-spectrum light is generated with a flash lamp; and the step of generating broad-spectrum light includes: providing an activation pulse to the flash lamp, the activation pulse having a pulse width that causes the flash lamp to emit the desired waveband while limiting emission of wavebands which the waveband filtering device is configured to filter out.

In some variations, the contaminant is not treated with any chemicals or contrast agents prior said emitting. In some variations, the step of filtering includes passing all but the desired illumination waveband of the broad-spectrum light through filter glass.

Variations of the systems, methods, techniques, devices, and components discussed herein may pertain to a method of identifying a contaminant on a substrate, the method comprising: emitting broad-spectrum illumination with a broad spectrum illumination source; first filtering the emitted broad-spectrum illumination with a first reflective optical filter configured to reflect a particular illumination waveband such that the first reflective optical filter reflects a first filtered illumination; second filtering the first filtered illumination with a second reflective optical filter configured to reflect the particular illumination waveband such that the second reflective optical filter reflects a second filtered illumination; emitting the second filtered illumination as an output illumination onto a target area on the substrate, where the output illumination in the particular illumination waveband causes the substrate to fluoresce in the visible spectrum but is absorbed by the contaminant; and determining whether a contaminant is present in the target area based on identified areas of fluorescence and absorption in the target area.

In some variations, a step of filtering includes dissipating those portions of the broad-spectrum illumination not reflected by the first reflective optical filter. In some variations, the broad-spectrum illumination source is a flash lamp having a particular illumination time profile and the step of emitting broad-spectrum illumination includes reducing a duration of an activation pulse driving the flash lamp such that the broad-spectrum illumination emitted by the flash lamp includes an increased proportion of ultra-violet (UV) wavelengths and a reduced proportion of visible and near-infra-red wavelengths.

In some variations, the step of determining includes capturing a visible-spectrum image of the illuminated target area with an imaging device. In some variations, the particular illumination waveband is a vacuum ultra violet (VUV) waveband and the contaminant is a latent fingerprint.

In some variations, the step of dissipating includes passing at least part of those portions of the broad-spectrum illumination not reflected by the first reflective optical filter through filter glass. In some variations, the step of dissipating includes including suppressing at least part of those portions of the broad-spectrum illumination not reflected by the first reflective optical filter with a baffle.

Further scope of applicability of the techniques, devices, and solutions described herein will become apparent from the detailed description given hereinafter. However, it should be understood that the detailed description and specific examples, while indicating preferred embodiments of the techniques, devices, and solutions described herein, are given by way of illustration only, since various changes and modifications within the spirit and scope of the disclosure will become apparent to those skilled in the art from this detailed description.

BRIEF DESCRIPTION OF DRAWINGS

The techniques, devices, and solutions described herein will become more fully understood from the detailed description given herein below and the accompanying drawings which are given by way of illustration only, and thus are not limitative of the present disclosure, and wherein

FIG. 2a depicts a variation of an illuminator for illuminating latent fingerprints as described herein;

FIG. 3b depicts a variation of filtering in a parallel mirror substrate as described herein;

FIG. 3c depicts a variation of filtering in a wedged mirror substrate as described herein;

FIG. 3d depicts variations of mirror substrate shapes and orientations as described herein;

FIG. 3e depicts a variation of an illuminator for illuminating latent fingerprints as described herein;

FIG. 3f depicts a variation of filtering in a light pipe substrate as described herein;

FIG. 5a depicts a variation of a portable latent fingerprint illumination and imaging device as described herein;

FIG. 5c depicts a variation of filtering in a prism substrate as described herein;

FIG. 5d depicts a comparison of mirror filtering and prism filtering as described herein;

FIG. 6 depicts a variation of an illuminator for illuminating latent fingerprints as described herein;

FIG. 7a depicts a variation of an illumination time profile for imaging latent fingerprints as described herein;

FIG. 7b depicts a variation of the flash lamp energy versus time for imaging latent fingerprints as described herein;

The drawings will be described in detail in the course of the detailed description.

DETAILED DESCRIPTION

The following detailed description of the invention refers to the accompanying drawings. The same reference numbers in different drawings identify the same or similar elements. Also, the following detailed description does not limit the techniques, devices, and solutions described herein. Instead, the scope of the techniques, devices, and solutions described herein is defined by the appended claims and equivalents thereof.

Figure 1A:
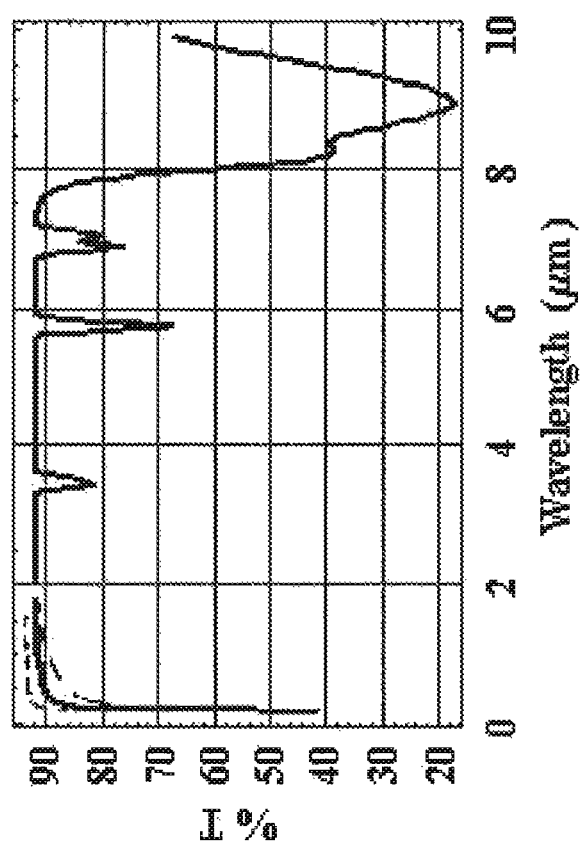
FIG. 1a depicts a variation of a transmission spectrum for imaging latent fingerprints as described herein.
Figure 1B:
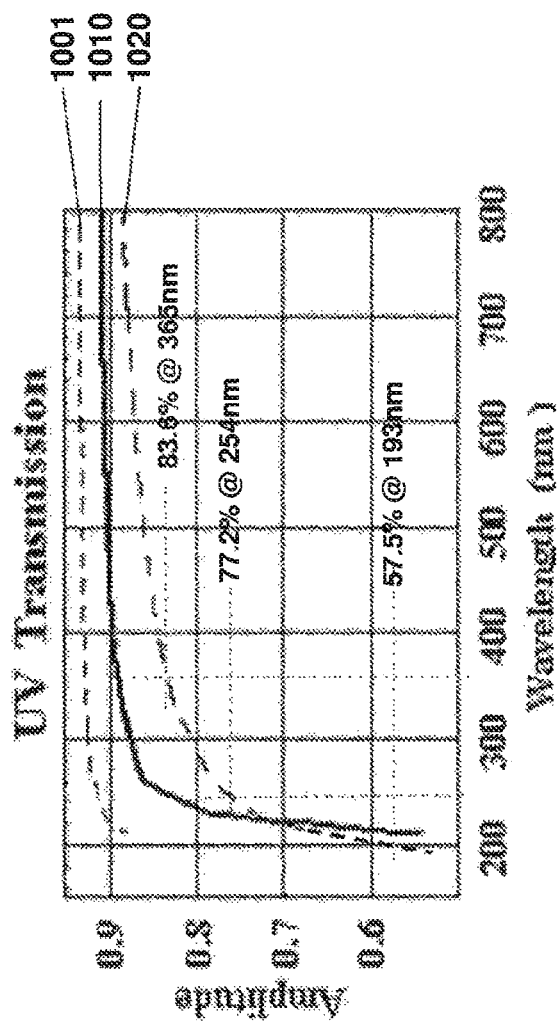
FIG. 1b depicts a variation of a transmission spectrum for imaging latent fingerprints as described herein.

For fingerprint oils/waxes, there are specific electro-optical radiation domains where absorption of the fingerprint oils/waxes significantly exceeds the absorption of a background material. The image contrast of latent fingerprints is directly linked, but not limited, to their absorption (scattering, for example, may also contribute to contrast). An absorption significantly exceeding the absorption of a background material means a level of difference in the absorption that allows for a contrast level sufficient to permit imaging/detection of the fingerprint. As shown in FIG. 1a, example domains are in the ~5.8 µm, ~3.5 µm, ~9 µm, ~7 µm, and less than ~0.5 µm ranges. This spectrum is for a specific fingerprint material, other materials suitable for such detection, such as contaminants or contraband, may have different absorption/transmission spectra. Furthermore, in some variations, at ultra-violet wavelengths, absorption produces higher contrast images if fluorescence is eliminated from the process. An example of absorption of various materials at ultra-violet wavelengths is shown in FIG. 1b. Specifically, absorption spectra for clean quartz 1001, forehead sweat 1010, and fingerprint oils/waxes 1020 are shown.

Using white paper and metal as an example surfaces/substrates, it can be seen that, a fluorescing surface (paper) shows some contrast at 365 nm and better contrast at 254 nm, whereas a non fluorescing surface (metal) shows some contrast at 254 nm and better contrast at 193 nm. In the context of this document, good contrast means a level of contrast that allows for visual identification of the presence of a fingerprint on the surface by a person or proper imaging device such as a camera with the appropriate lens.

The effect of fluorescence in background materials such as paper is triggered, at least in part, by short wavelength illumination. Surfaces such as paper fluoresce more strongly, in a wider band, and for a longer time than organic contaminants (such as latent fingerprints) that may be deposited thereon. Since fluorescence typically acts as background noise, a light source and image filter should preferably be chosen to eliminate some or all of such fluorescence for noise reduction purposes.

Figure 1C:
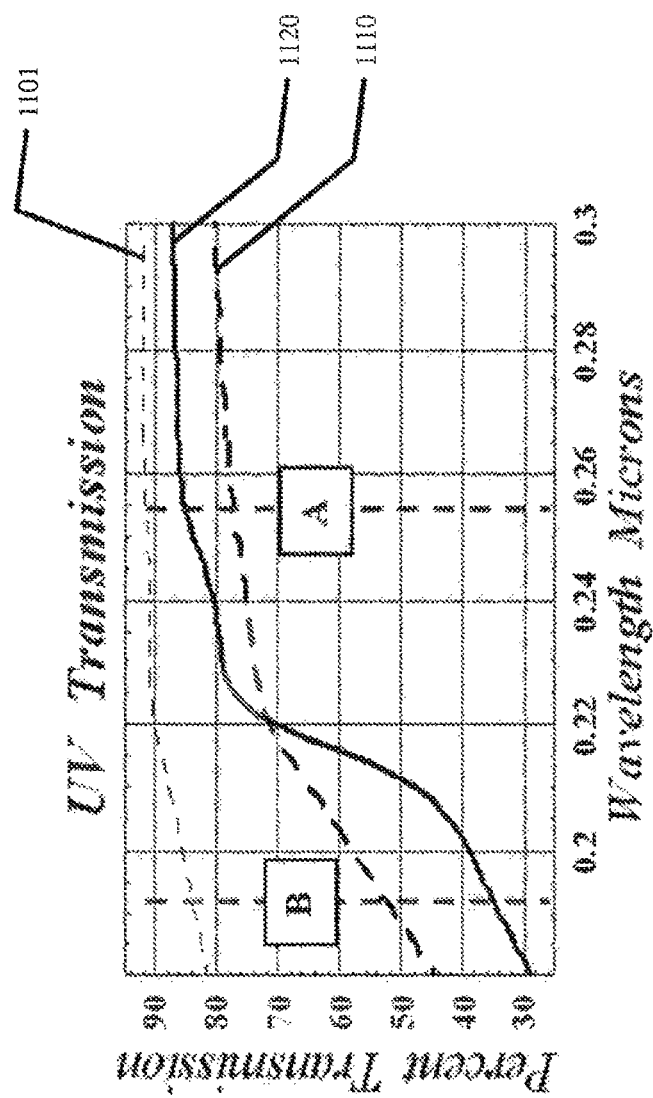
FIG. 1c depicts a variation of a transmission spectrum for imaging latent fingerprints as described herein.

Since fingerprint oil has moderate absorption at 254 nm, eliminating paper fluorescence, which may occur in the visible spectrum, will generate an image using only absorption by the fingerprint oils. By choosing a wavelength of light illuminating the fingerprint that coincides as much as possible with the maximum optical absorption of the fingerprint material as shown in FIG. 1c, the material under the fingerprint cannot fluoresce because the illumination does not pass through the fingerprint oils/waxes, FIG. 1e shows the absorption profiles for clean quartz 1101, forehead oils 1120, and finger/hand oils 1110. As can be seen in the figure, A shows absorption for head and finger oils 1110, 1120 at 254 nm in the range of about 15% to 24%. B shows absorption for head and finger oils 1110, 1120 at 193 nm the range of about 47% to about 65%.

Figure 1D:
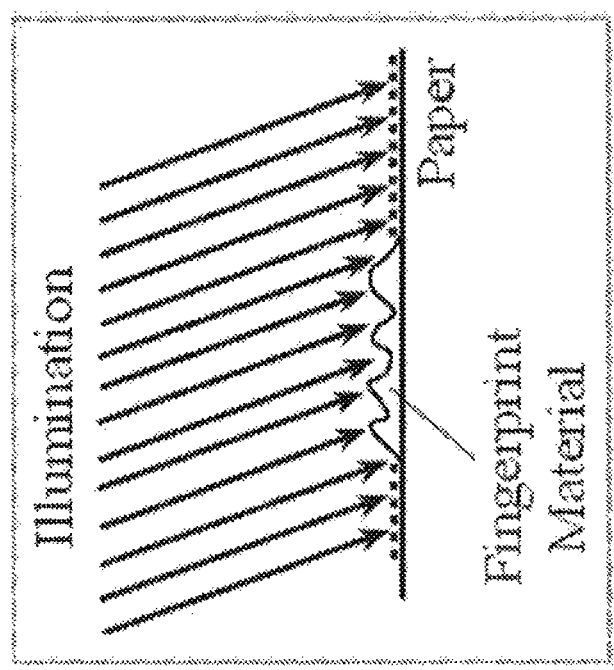
FIG. 1d depicts a variation of latent fingerprint imaging as described herein.
Figure 1E:
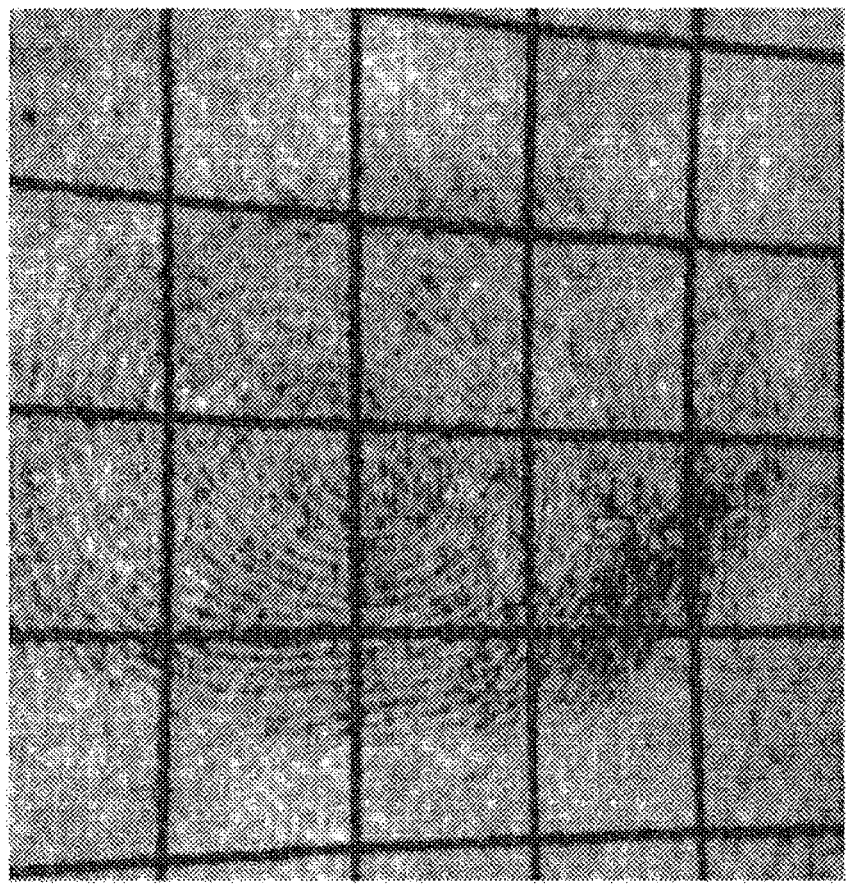
FIG. 1e depicts a variation of an image of a latent fingerprint illuminated and captured as described herein.

As shown in FIG. 1d, in variations using an illumination such as one in the range of 193 nm, the paper or other fluorescent, fingerprint-bearing substrate not covered by the fingerprint oils/waxes does fluoresce (represented by dotted lines), creating contrast to the fingerprint ridges and making them appear dark (no dotted line present) while the rest of the substrate appears light/fluorescent. Such variations allow for fingerprints to be readily and easily detected or otherwise discerned in the visible spectrum against the background fluorescence of the fingerprint-bearing substance. In the case of non-fluorescent substrates (such as clean metal), visible spectrum detection of fingerprints using such illumination techniques is also possible.

In some variations, detection may be accomplished by a human observing the illuminated surface and seeing whether or not fingerprints are present. In other variations, a visible-spectrum detector, such as a digital camera, film camera, video camera, photodetector or other visible-spectrum electro-optical radiation detector may be configured to image a surface being illuminated for fingerprint detection. In some variations, such a camera or detector may be combined with, coupled to, or otherwise providing image data to downstream data processing devices or systems that may perform analysis or identification processes on one or more of the detected fingerprints in the field of view of the camera or otherwise included in the image data captured by the detector.

In some variations, absorption may continue downward to at least 180 nm and possibly farther. In some variations, image contrast detection and sensitivity increase as the illumination wavelength decreases, but new issues may arise such as atmospheric absorption. For wavelengths below 185 nm, for instance, a nitrogen purge becomes necessary because other atmospheric components may absorb the illuminating wavelengths.

As noted above, illumination with light wavelengths of between 190 and 200 nm allow for imaging of fingerprints with regular, visible-spectrum cameras. The fluorescence of the substrate material (such as paper) provides visible spectrum contrast against the fingerprint, which does not fluoresce (or fluoresces very weakly) and therefore appears dark in the visible spectrum where the substrate fluoresces. The picture shown in FIG. 1e, for example, was captured using a camera on a mobile phone while the fingerprint-bearing paper was illuminated with 193 nm light.

Although lasers are a common source of short-wavelength light (an ArF laser, for instance, can produce 193 nm light), any short wavelength light source may be used to generate the desired wavelength ranges for illumination. A filtered flash lamp, for instance (such as, for example, a xenon lamp with a quartz window), can be made to produce illumination in the 190-215 nm range. An example of such a filtered flash lamp arrangement is shown in FIG. 2.

In the arrangement shown in FIG. 2a, a flash lamp 2001 is reflected off of two band-specific mirrors 2050, 2010 and the resultant light is used to illuminate a fingerprint-bearing substrate. The band-specific mirrors may, in some variations, be dielectric band-specific mirrors that reflect only the desired illumination wavelength or wavelength range (such as, for example, ~193 nm, ~200 nm, or wavelength ranges that include one or more of such wavelengths) and transmit all other wavelengths. The mirrors 2050, 2010 may be equipped with baffles 2020, 2060 that capture and absorb or otherwise block or suppress those wavelengths not reflected by the mirrors 2050, 2010. The entire illumination reflection assembly may also be disposed behind a baffle 2030 (such as, for example, a screen, a beam tube, a baffle, or a closed box) so that only the desired wavelengths of light 2040 may illuminate a target substrate.

It should be noted here that any substrate having contaminants thereon where there is a suitable difference between the absorption spectrum of the contaminant and the substrate can be imaged in this way by proper selection of illumination wavelengths. Any oily residues, for instance, having roughly the same composition as fingerprint oils/waxes, can be detected/imaged in this way. Similarly, other contaminants such as blood, oil, "invisible" ink, industrial pollutants, and, in some cases, unwanted atmospheric contaminants (i.e. particulate matter inside a cleanroom) may be illuminated for visible-spectrum (or other spectral regime) detection. Furthermore, it should be noted that such latent fingerprint/contaminant detection is realized without the use of additional chemicals or substances that may alter or otherwise damage/destroy the fingerprint or contaminant. Detection as described herein is realized through illumination with an appropriate illumination waveband without requiring that the target surface be treated or otherwise exposed to chemicals or contrast agents to enable imaging.

The variation shown above with band-specific mirrors is preferable to band-pass filter coatings because most existing short-pass VUV (vacuum ultra-violet) filters have comparatively poor performance. Some may have low transmission, some may have a sloping cut-off, and some may turn back "on" at longer wavelengths (e.g. they may be fully transparent again at infra-red wavelengths).

VUV dielectric mirror coatings, by contrast, are preferable because they are configured to reflect only a particular waveband. They tend to have high reflection, sharp cut-off, and do not pose the problem of turning back "on" at unexpected wavelengths because they are transparent at all wavelengths other than the reflective ones. VUV dielectric mirror coatings are preferably made from materials or compounds, or combinations thereof, that show high reflection for the desired VUV wavelength(s) or wavelength range(s). Variations of VUV dielectric mirror coatings may include materials such as AlF3, MgF2, Na3AlF6, GdF3, chiolite, DyF3, cryolite, BaF2, NdF3, LIF, YF3, MgO, TiO2, SiO2, Nb2O5, Al2O3 and/or combinations thereof. Such coatings may be deposited onto glass, quartz, sapphire, fused silica, ALON or other materials that are transparent or otherwise not highly reflective in the visible spectrum.

In some variations, a mirror substrate may be equipped with a VUV coating on its front, or 'mirror' side and art anti-reflective or non-reflective coating on its back side. A non-reflective coating may be preferred to transmit light not intended for reflection by the VUV mirror coating. An anti-reflective coating may be preferred to enhance transmission of non-reflected light through the mirror and into, for example, a baffle or light box or other optical absorption device or medium to prevent unwanted light from illuminating the target.

Figure 2B:
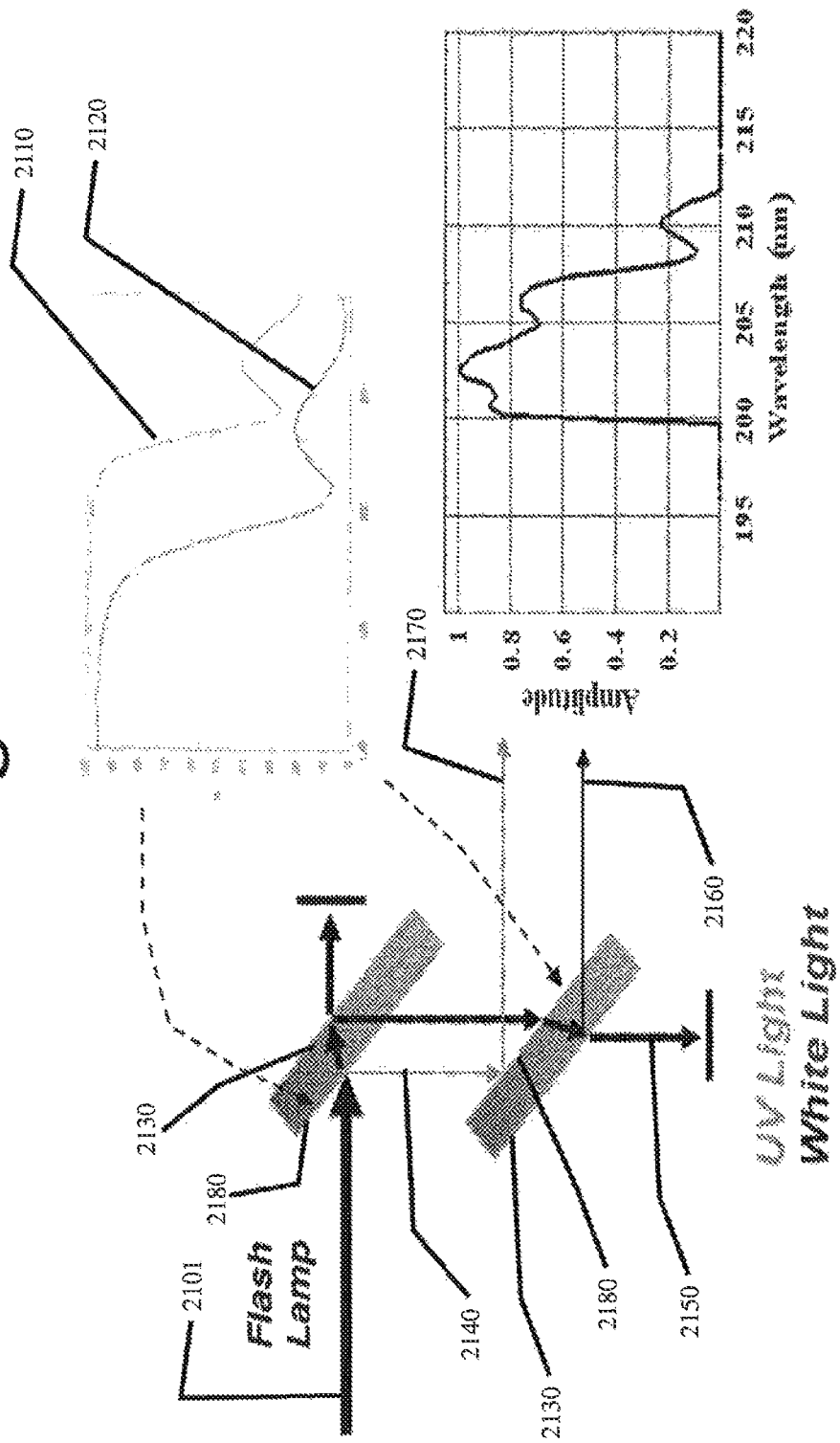
FIG. 2b depicts a variation of an illuminator for illuminating latent fingerprints as described herein.

Using mirror coatings as a VUV filter can be accomplished with, for example, a xenon flash lamp light source, in the manner shown in FIG. 2b. In the variation shown in FIG. 2b, light from a flash lamp 2101 includes both white (broad spectrum) light and the desired illumination wavelength(s). Mirror coating reflection spectra 2110 and 2120 show performances at two orthogonal polarizations. Nonpolarized light, such as that coming from a flash lamp, will have a reflection spectrum that is roughly the average of these two. The desired illumination wavelength(s) 2140 reflect off of the mirror coating(s) 2180 and generate the desired illumination output 2170 for fingerprint detection. The white light 2150 passes through the mirror coating 2180 and reflects off the back surface of the mirror 2130. This reflected white light 2160 acts as background noise and should preferably be reduced or eliminated. While multiple reflections on coated/band-specific mirrors may reduce the amount of white light eventually reaching an illuminated surface, it is more preferable to find a simple method to eliminate the light noise entirely instead of adding more mirrors to the optical path. This is because at a certain point, the mirrors will, through reflection/transmission loss, prevent a useful amount of the desired wavelength from reaching the target. Also, in variations using a flash lamp illumination source, the flash lamp light is also rapidly spreading/diverging. Minimizing the path length from the flash lamp to the sample surface may produce a higher illumination flux (energy per area), which may be required for some poorly performing samples.

Figure 3A:
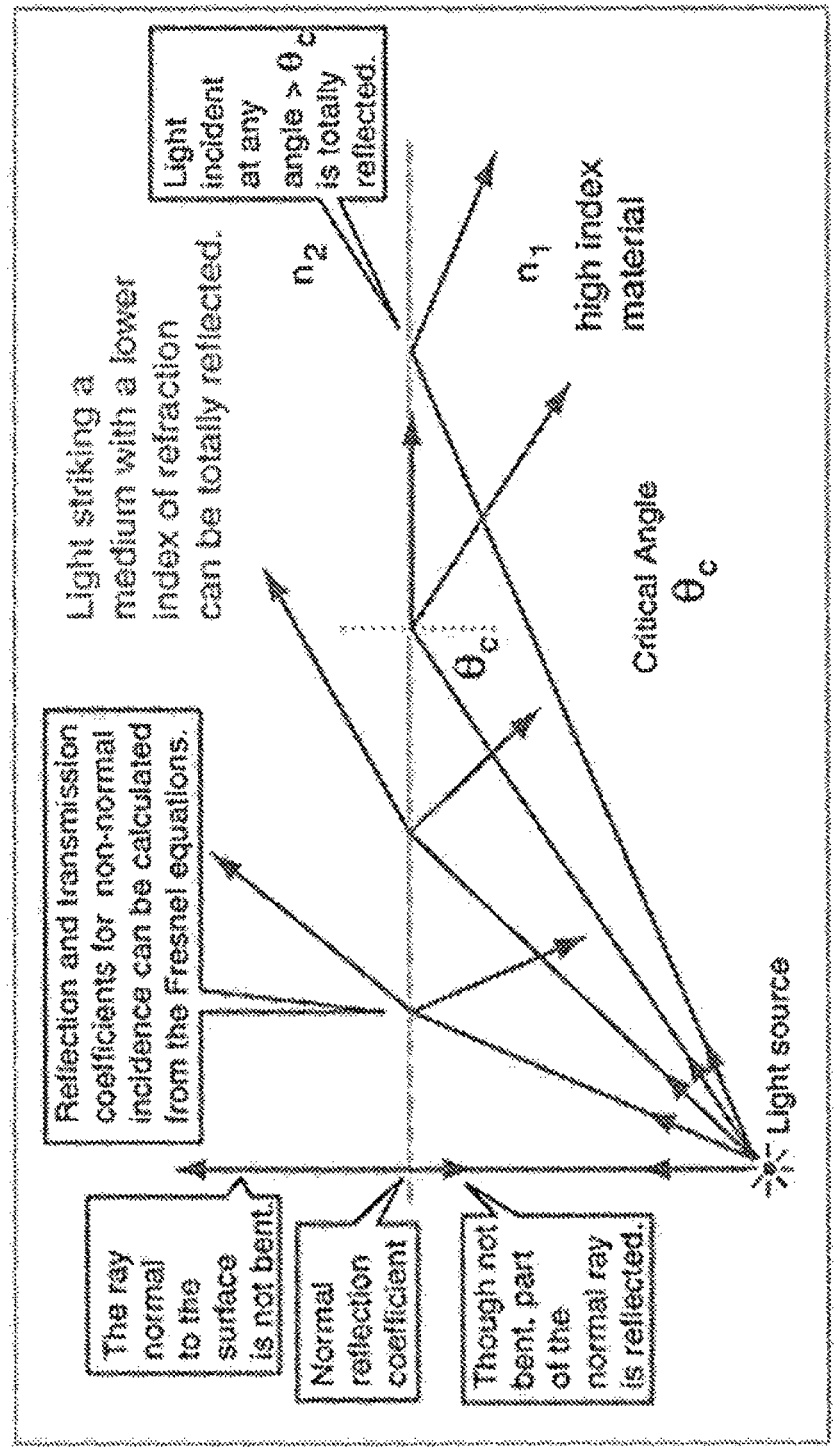
FIG. 3a depicts a variation of when Total Internal Reflection (TIR) occurs within a medium.

As shown in FIG. 3a, when light travelling in a medium of higher index of refraction is incident upon a medium of lesser index of refraction, the ray exiting the higher index medium is bent away from the normal, so the exit angle is greater than the incident angle. As the incident angle increases the exit angle will approach 90° for some critical incident angle θc, and for incident angles greater than the critical angle there will be total internal reflection (TIR).

The critical angle can be calculated from Snell's law by setting the refraction angle equal to 90°. For any angle of incidence less than the critical angle, part of the incident light will be transmitted and part will be reflected. The normal incidence reflection coefficient can be calculated from the indices of refraction. For non-normal incidence, the transmission and reflection coefficients can be calculated from the Fresnel equations.

In some variations, mirror substrates may be shaped to cause such total internal reflection (TIR). Such TIR shaping may be useful for preventing the reflection/transmission of light that passes through the reflecting coating portion of a mirror and strikes the back surface of the mirror (such as, for instance, a mirror created by coating a substrate with a band-specific reflective coating). In some variations, a mirror is a body having two reflecting surfaces—a front surface and a back surface. Some light reflects off the front surface of the mirror, other light passes through the front surface and reflects from the back surface. A variation of a parallel mirror surface is shown in FIG. 3b. In the variation shown, the mirror has a front surface reflection 3101. In the case of a substrate coated with a VUV reflective coating, this front surface reflection is the desired illumination wavelength for fingerprint detection.

The mirror may also have a back surface reflection 3110 at the same angle as the front surface reflection 3101. In the case of a substrate coated with a VUV reflective coating, this back surface reflection 3110 may be white light or other light noise that interferes with or otherwise reduces the effectiveness of a fingerprint detection process that uses the desired illumination wavelength(s). Also, in some variations, light may escape out the back of the mirror 3120. It is desirable to reduce or eliminate the back surface reflection 3110 in a mirror equipped with a VUV-reflective coating in order to improve the fingerprint detection process facilitated by ultraviolet illumination of fingerprint-bearing substrates.

In a wedged mirror configuration, however, the front and back surface reflections do not exit the mirror at the same angle. In fact, as shown in FIG. 3c, for some wedge angle configurations, total internal reflection (TIR) can be achieved for the reflection from the back surface 3220, thereby eliminating unwanted light coming from the back surface of the mirror and allowing for only the front surface reflection 3210 to be transmitted reflected to a downstream optical component and/or target.

As shown in FIG. 3d, a wedged substrate with the wedge oriented to decrease internal reflection angle is a preferable configuration for reducing light noise in a fingerprint illumination/detection system that employs wavelength-specific mirrors to generate desired illumination wavelengths. As can be seen in the figure, a parallel mirror substrate 3300 equipped with a front-side mirror coating 3330 and, in some variations, a back-side anti-reflection coating 3340 may nonetheless reflect some portion of incident white light from the rear surface of the substrate. Because of the parallel substrate configuration, the unwanted reflection has the same angle as the desired reflection (in this case, the VUV light). A wedged mirror substrate 3310 oriented to increase internal reflection angle may cause unwanted light 3370 to be reflected at a different angle from the desired illumination wavelength(s) 3380. However, such an arrangement may nonetheless allow the unwanted light 3370 to be reflected onto the target or otherwise create unwanted light noise that interferes with the latent fingerprint detection wavelength(s) and therefore impairs or reduces the effectiveness of the fingerprint detection process.

Using a wedged substrate 3320 oriented to decrease internal reflection angle, however, allows for the desired wavelengths to reflect from the mirror coating 3360 whereas any unwanted light that does not pass through the anti-reflective coating 3350 on the back side of the substrate is substantially captured inside of the wedged substrate 3320 and directed down the length of the wedge, preventing it from interacting with the desired reflection wavelength(s) and allowing the noise light to be directed into a baffle or other light-blocking device that prevents it from interacting with or otherwise illuminating a fingerprint detection target surface.

Using such wedge-shaped mirrors, it becomes possible to almost completely eliminate reflections from the back surfaces of the mirrors, as shown in FIG. 3e. In the configuration shown, light from a broad-spectrum flash lamp 3400, such as a xenon flash lamp, may be directed to a first wedged substrate 3460 coated with a VUV mirror coating 3410. The desired VUV wavelength(s) may be reflected from the front surface of the wedged substrate 3410 whereas the remaining light, which is noise, may pass through or down along the wedged substrate 3460 to be captured by a baffle 3420 that prevents light from reaching an illumination target. In some variations, the wedged substrate 3460 may be equipped with an anti-reflection coating 3470 on its back, or non-mirror-coated side to reduce the amount of white light that is reflected by wedged substrate 3460 and thereby better capture the unwanted light wavelengths in the baffle 3420. In some variations, a second wedged substrate 3450 may perform a second such reflection operation on the light reflected from the first wedged substrate 3460 to further reduce the amount of light noise in the filtered light 3430 directed to the fingerprint detection target. In some variations, such an arrangement may be disposed inside a light-proof or otherwise opaque container or device such that broad-spectrum illumination 3400 may enter the container at one aperture and filtered light 3430 may exit the container at another aperture.

In some such variations, because the dielectric VUV coating does not "turn back on" at longer wavelengths, using such coatings permit a wide-band light to be used as a VUV source. Some variations of such a solution may therefore permit the use of COTS (commercial off-the-shelf) illumination and imaging devices in conjunction with the properly configured filtering/reflective elements. Illumination devices may include flash lamps as described above and/or other illumination sources having a VUV spectral component in their illumination output. Imaging devices may include visible spectrum detection devices such as digital cameras, film cameras, or other conventional visible-spectrum detection devices. (Band-pass reflection coatings can be made for any portion of the optical spectrum. This filter can be made to operate in any regime of the optical spectrum, not just a high-pass UV filter.)

In one variation, an illumination source may be configured to illuminate a target for a predetermined duration or intensity operating in concert with an imaging device that captures images of the illuminated target. In the case of digital imaging devices such as digital cameras, the captured images may then be evaluated or otherwise analyzed for fingerprint detection and analysis. In another variation, the illumination source may be operated or used independently of an imaging device and/or in concert with a video/image feed, allowing a user of the illumination source and/or video feed to visually ascertain whether latent fingerprints are present on a target area. In some variations, such a video or image feed may be live, in other variations, the video or image sequence may be recorded for later viewing. In yet further variations, a camera may be omitted entirely, with an observer directly viewing an illuminated target area to visually discern whether or not fingerprints/contaminants are present therein.

Optical Filters

With respect to the coating itself, it is preferable to have art efficient optical filter coating, preferably for the VUV portion of the spectrum, with 80% or more optical transmission and reasonably sharp cut-offs. In some variations, a sharp cut-off is only required for the long wavelength side of the spectrum. Such a coating may be used in conjunction with a broad-spectrum illumination source, with the filter selecting only a portion of the illumination spectrum and effectively discarding the rest of the spectrum at a high extinction.

As noted above, reflective coatings are a preferred solution for such a filter element. Typical optical filters act on transmission effects, hand-pass, low-pass, high-pass etc. Mirrors and/or mirror coatings, by contrast, act on reflection. Typical optical filters are inefficient in the VUV portion of the spectrum, (e.g. 20% peak transmission or less) whereas VUV mirror coatings may have up to 80% or more optical reflection. In some cases, such mirrors may show reflection of up to 95% or better. Furthermore, as mentioned above, some such transmission or hand-pass filters 'turn back on' at longer wavelengths on the presumption that they're not to be used with a truly broad-spectrum illumination source.

Reflection coatings work well when restricted to limited regimes of operation. As shown in the variations of FIGS. 2a and 3e, a wide-band source illuminates the coating which reflects the design wavelengths into a specific direction where the light will be used. The light that is not in the desired reflection hand of the coating is preferably prevented from entering the optical system, where it otherwise acts as background noise.

In the variation shown above in FIG. 3e (and also in other solutions, such as prism-based solutions) the shape of the mirror substrate is used to redirect the background light (noise) from the path of the design wavelengths. The redirected light (noise) is easily baffled away from the design wavelengths because the paths of the noise can be designed to be different than the paths of the design wavelengths.

In some solutions, the substrate design may also act as a light pipe containing the design wavelengths. This is helpful when the light source has a wide divergence. In such variations, the light exiting the source may be effectively captured and channeled to the output of the filter substrate because the filter mirror coatings are deposited on orthogonal sides of this substrate. The noise in such variations may exit the substrate in all directions but the design wavelengths will travel down the length of the substrate. Such a filter is designed to impose multiple internal reflections on the incident light. Each reflection may act as a large attenuation to the noise but not to the design wavelengths. One such variation of a substrate design in shown in FIG. 3f.

In the variation shown, VUV illumination is desired as an output signal 3540. White or broad-spectrum light 3500 is therefore transmitted into an input face 3560 of a VUV transparent/transmitting substrate material 3530 such as quartz or calcium fluoride. In the variation shown, the input face 3560 is not coated with a filter or mirror coating, allowing all wavelengths to enter the substrate 3530. In the variation shown, white light 3500 entering the input face 3560 of the substrate is directed towards a side of the substrate. The side, in the variation shown, is coated with a hand-specific dielectric mirror coating 3510 that is configured to reflect one or more VUV wavelengths while transmitting other wavelengths through the coating. The light reflected from the first coated side 3510 may then be directed to a second coated side 3550 of the substrate. In the variation shown, the second coated side 3550 is also equipped with a hand-specific dielectric mirror coating configured to reflect one or more VUV wavelengths while transmitting other wavelengths through the coating. In other variations, the coatings on each side of the substrate 3530 may have different properties. In one variation, one coating may reflect a narrower waveband than the other coating. In another variation, the coatings may be selected such that they have an overlapping wavelength range, thereby allowing narrow waveband filtering using broader waveband mirror coatings.

The number of reflections (and therefore number of filtering operations) performed on the input light 3500 may depend on the length of the substrate 3530 and angle of the sides 3550, 3510. The filtered light 3540 may exit such a "light pipe" though an output face 3520 that may also be un-coated or otherwise not configured to further filter the light signal 3540. Such "light pipe" variations may provide improved noise reduction and reduced complexity by allowing for multiple reflection-based filtering passes/operations within a single mirror element. Furthermore, such "light pipe" filters may be designed to limit light divergence, allowing the filter to shape the output light from the flash lamp and direct more light to the target.

Figure 3G:
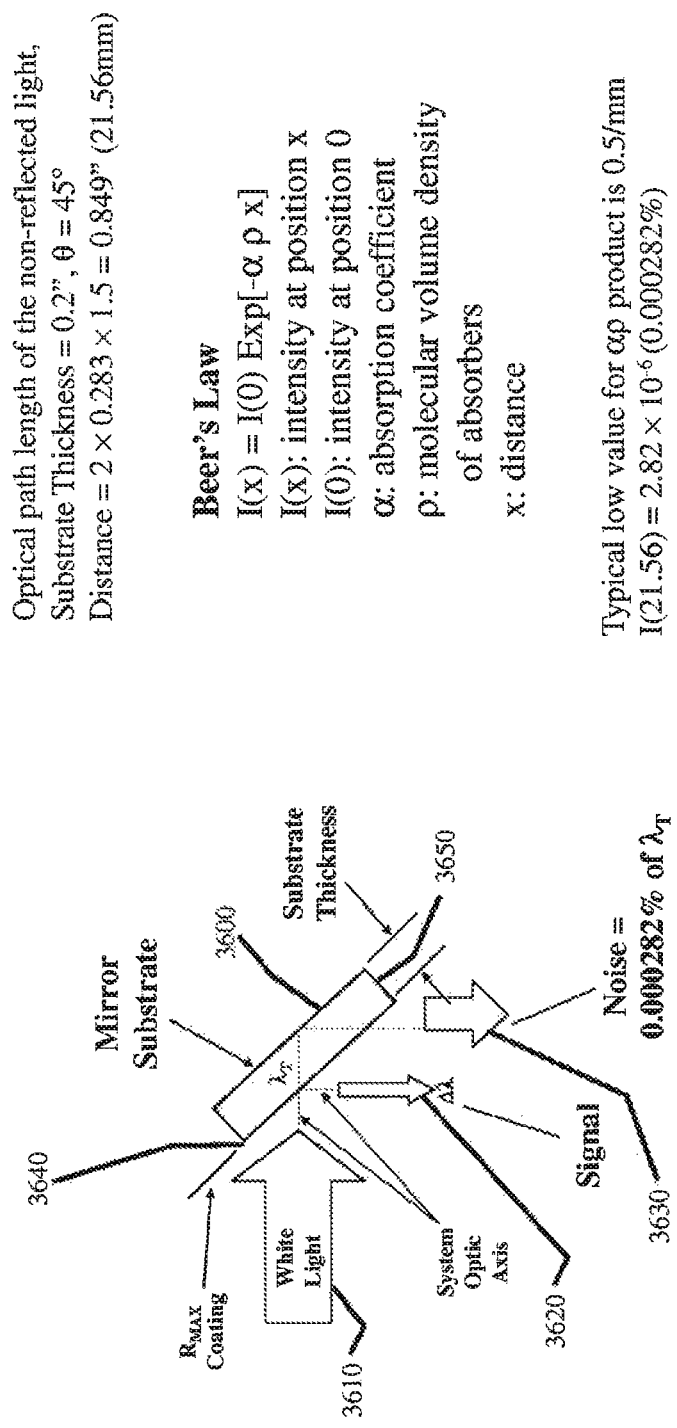
FIG. 3g depicts a variation of filtering in an absorptive substrate as described herein.

Other solutions for providing noise extinction include back-side mirror coatings and/or attenuation filters. In some variations, the mirror substrate is used to attenuate the background light (noise) by optical absorption. The substrate can be made from a material that will absorb the light not reflected by the mirror coating. The above-discussed reflection filter (or similar filter solutions) separates wide band incident light into the design/desired wavelengths and all the rest (noise.) The wideband light, or noise, that passes through the VUV dielectric coating is absorbed by the substrate, which is actually an attenuation filter. The optical density of this filter can be very high, effectively reducing the noise to negligible levels. Such a variation is shown in FIG. 3g.

In the variation shown, white light or other broad-spectrum light 3610 may be directed to a substrate 3600 equipped with a dielectric band-specific mirror coating 3640 that is intended to reflect the desired waveband(s) as a filtered optical signal 3620. The substrate may be made of a particular material, having a particular thickness 3650, that is meant to absorb some or all of the light outside of the desired signal 3620 waveband(s). Some such substrate 3600 variations may be made of filter glass such as the dark glass found in some sunglasses. Other variations may be made of colored glass or other selectively absorbing material(s). In some variations, a small amount of the undesired light may nonetheless escape as noise 3630, but the amount of noise may be significantly reduced due to the photo-absorbing substrate material 3600.

In the variation shown, the substrate 3600 is depicted as having a thickness of 0.2" and being oriented at an angle of 45 degrees with respect to the incoming white light 3610. Such a variation may maximize the distance traveled by light inside the substrate, thereby maximizing opportunity for absorption within the substrate. Other variations may use different thicknesses and angle orientations depending on desired effect(s). In some variations, such an absorbing substrate may be combined with a wedged TIR configuration to realize benefits of both TIR and in-substrate noise absorption.

In some variations, absorbed light may cause the substrate to fluoresce. In some variations, such fluorescence may itself become a noise source. In other variations, such fluorescence may have little or no effect on the output signal 3620 depending on the desired output signal wavelength(s). Variations using longer wavelengths, such as variations meant to operate in MWIR or LWIR wavebands, may be unaffected by fluorescence effects of the substrate.

LW Illumination/Filtering

Figure 4:
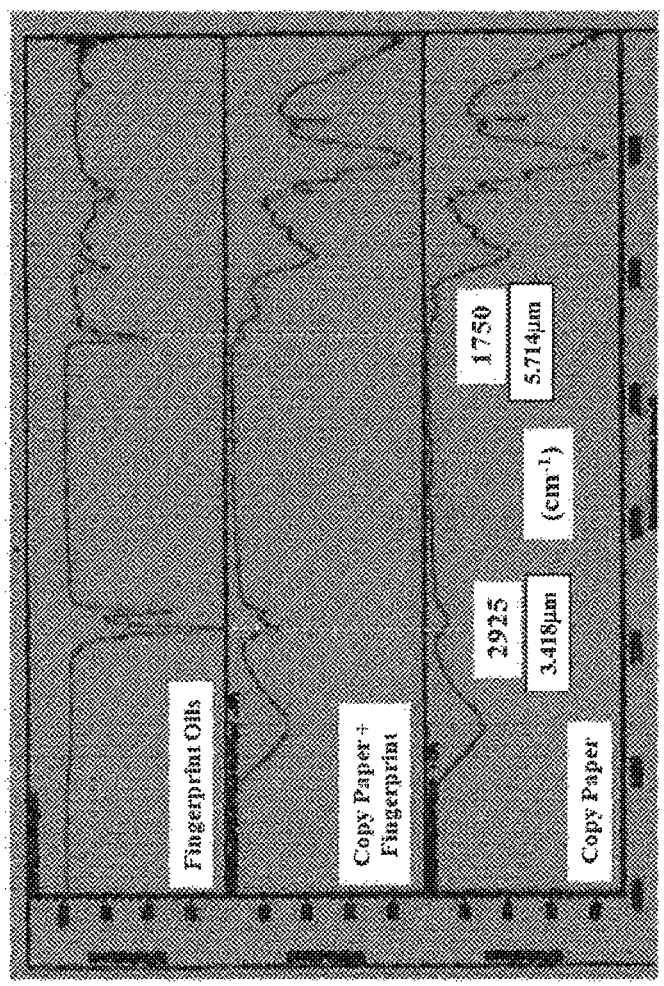
FIG. 4 depicts a variation of a transmission spectrum for imaging latent fingerprints as described herein.

Although discussed above with respect to VUV wavelength illumination, detection of latent fingerprints on a surface may also be realized with long-wavelength illumination (MW to LW IR), removing some of the issues associated with fluorescence. In the MWIR to LWIR spectrum, 3.418 and 5.714 µm are two wavelength regions showing spectral features for a particular fingerprint material in fingerprint-bearing copy paper that are distinct from normal copy paper, as shown in FIG. 4. Spectral features for other fingerprint materials or other contaminants may be different than those shown in FIG. 4. Solutions using infrared illumination may require detectors configured to detect such infra-red illumination. Since a substrate illuminated with MWIR/LWIR may not fluoresce significantly, visible spectrum differentiation/detection of fingerprint-bearing and/or contaminant-bearing (in variations where something other than and/or in addition to fingerprints is being detected) areas may not be facilitated. Such variations may require an MWIR and/or LWIR detector or detection device to observe a target area subject to such illumination.

In some such variations, illumination sources and mirror coating arrangements of the types shown in FIGS. 2a and 3e may be utilized, with the mirror coatings being selected for MWIR and/or LWIR reflection and the illumination source being selected such that it has an MWIR and/or LWIR component in its output illumination. In other variations, an MWIR or LWIR laser may be used to provide illumination. Such solutions, while costlier, may provide illumination and detection capability at significantly longer ranges, such as at distances of 10 feet away or more. In some cases, at distances of over 30 feet away. In some variations, distances of over 60 feet or more may be realized. Some variations may work at even greater ranges, such as distances sufficient to perform imaging across multiple-lane roads or to allow imaging of ground targets from aerial vehicles. In some such variations, a collimated/directed illumination source, such as an MWIR/LWIR laser source, coupled with an MWIR/LWIR detector may provide Fingerprint/contaminant detection capability that can be vehicle-portable and unobtrusively deployed for tasks such as scanning fingerprints on the door handle of a car parked across the street. Such variations are limited in detection range and capability only by the effective range of the illumination source and the sensitivity/capability of the associated detector.

Portable System

In some variations, an illumination source and filtering assembly may be embodied in a portable and/or small-sized, self-contained unit. One variation of such a portable unit-configured to operate with a camera, is shown in FIG. 5.

In the variation shown, a camera 5000, which may be a commercially available digital and/or film camera, may be mounted to/on a camera holder 5050. The camera holder 5050 may be joined, attached, or otherwise combined with a flash lamp holder 5060 designed to hold a flash lamp providing illumination that include VUV spectrum illumination.

The variation shown in FIG. 5a uses a band-pass filter 5040 coating to select for VUV spectrum illumination and prisms 5030, 5020 for subsequent noise reduction/filtering. In some variations, a band-pass filter may be used simply as an initial filter to reduce the amount of longer-wavelength noise that the reflective elements must filter out/attenuate. In other variations, a band-pass filter may be omitted or replaced with some other waveband selecting element.

In some variations, prisms 5030, 5020 may be used in conjunction with band-specific reflective coatings that will reflect desired wavebands of VUV illumination while allowing noise wavebands to enter the prisms for additional reflection/attenuation and extinction. In other variations, one or both of the prisms 5020, 5030 may be replaced with coated mirrors having either a flat or wedge-shaped configuration as discussed above, or with light-pipe type solutions as discussed above.

Figure 5B:
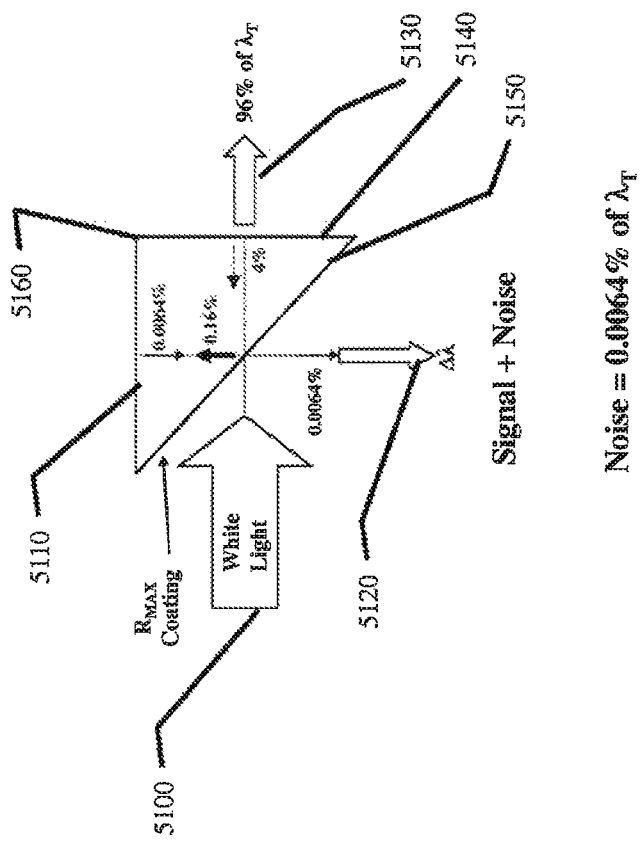
FIG. 5b depicts a variation of filtering in a prism substrate as described herein.

The coatings on reflective and/or refractive elements 5020, 5030 may be variations of the reflective filter coatings discussed above. The variation shown uses at least two prisms (or other reflective elements) so that the noise portions of the illumination source are further attenuated by additional reflections. A variation of a prism-based filtering solution is shown in FIG. 5b.

In the variation shown, a 90 degree turning prism 5160 is used as the optical substrate. In the variation shown, the prism 5160 includes two un-coated surfaces 5110, 5140, and one surface coated with a dielectric band-specific mirror coating 5150. The mirror coating 5150 is directed to accept incoming light 5100, which may be white light or may be already filtered light from an upstream filtering element. At the mirror coating 5150, those wavebands of the incoming light 5100 reflected by the coating are reflected as a signal portion 5120. The remaining portions of the incoming light 5100 either pass through the prism 5130, exiting through one of the un-coated sides 5140, or are attenuated through internal reflection before exiting the prism. In some such variations, noise may be reduced to a nearly negligible amount in the output signal 5120. The variation using a 90-degree turning prism shape has a filtering effect similar to that of using three mirrors in terms of noise reduction.

Another variation of prism-based filtering is shown in FIG. 5c. As can be seen from the figure, broad-spectrum light encounters a VUV mirror coating at a first reflection point 5240 on the prism. Light not reflected by the mirror coating passes through the first reflection point and comes to a second reflection point on the prism 5200. At this point, in the variation shown, 4% of the light is internally reflected within the prism whereas the remainder exits the prism at this point. Such a reflection process is repeated at second 5210 and third 5230 reflection points, with 4% of the light incident at the reflection point being reflected and the rest exiting the prism. The result is that white noise propagating into the system is greatly attenuated by the prism. An example of the difference between white noise attenuation of a single mirror element and a single prism element is shown in FIG. 5d.

In the variation shown, a mirror equipped with a dielectric, band-specific mirror coating 5340 produces a desired output signal 5300, but also generates noise 5310. In mirror-based variations, arrangements of two or more mirrors are preferred to reduce the amount of noise generated in an output illumination. By contrast, a prism equipped with the same dielectric, band-specific mirror coating 5350 generates a desired output signal 5320 but produces a significantly reduced amount of noise 5330. In the variation shown, the prism shape creates an effect similar to using three mirrors, substantially reducing the amount of noise included in an output illumination.

Although the variation shown in FIG. 5a uses two prisms, other variations may use more or fewer filtering elements. Some variations may combine prisms, mirrors, and/or other filter elements. Some variations may operate with only a single prism/mirror, and some variations may operate with no reflective elements at all—instead relying on especially precise/effective band-pass filter(s). Some variations may employ prisms made of optically absorbing materials to further attenuate noise being reflected inside the prism.

The light source, disposed in the flash lamp holder 5060, may be a xenon lamp of the type discussed above or may be any other light source having, in its emission spectrum, the appropriate wavelengths of VUV light. The light source may be coupled to a lamp driver (not shown) that drives the lamp and controls its operating/illumination frequency.

Furthermore, a battery or battery pack or some other external power source/supply may be provided in conjunction with the portable system shown above. This may be used to power the lamp driver and light source. In some variations this may also be used to power the camera. In other variations, the camera may have an independent power source such as an internal battery/battery pack.

The flash lamp assembly may have a flash lamp portion, a pulse forming network (PFN) that governs a pulse/illumination frequency of the lamp, a trigger circuit 5010 that controls the PFN, and a hot shoe that allows the trigger circuit to interact/connect with the camera and/or with the lamp driver. Other variations may realize connection/communication between the lamp/lamp driver and the camera without a hot shoe connection.

Thermal Load

In some variations, a flash lamp such as a plasma flash lamp may be used as the illumination source. Plasma flash lamps produce intense broad band output. Usable energy in the UVC portion of the optical spectrum (100 nm-280 nm) is available. In an optical filtering configuration, the output of a broad-spectrum (160 nm to >1000 nm) flash lamp can be divided into two wavelength bands—UVC and Visible to NIR. In order to separate UVC and VIS-NIR spectral outputs, a filtering arrangement as shown in FIG. 2a or 3e can be used.

In one variation of a filtering arrangement configured to discriminate between UVC and VIS-NIR illumination, shown in FIG. 6, flash lamp 6000 output may reflected off three ND (neutral density) filters F1, F2, F3, each with a maximum reflectance coating from about 185 nm to about 200 nm on the sides facing the flash lamp. In one variation of the arrangement shown, wavelengths <206 nm (UVC) may be reflected with almost 97% efficiency. Wavelengths >206 nm to 390 nm may pass through the reflectance coating and be almost completely absorbed in the glass substrate. Wavelengths >390 nm (VIS to NIR) may pass through the reflectance coating and be partially absorbed in the substrate. In the variation shown, enough VIS to NIR light passes through F1 to produce a signal on detector D1. Detector D2 reads the UVC light coming from the flash lamp. Both detectors are identical with ns reaction times and response from 200 nm to 1100 nm. Although depicted in a testing configuration that detects VIS-NIR and UVC output levels, such a configuration may be used, without the detectors D1, D2, to generate filtered UVC output illumination for latent fingerprint/contaminant detection.

The signal output and duration of the UVC and VIS-NIR portions are shown in FIG. 7a, with UVC shown as a dashed line and VIS-NIR as a solid line. In the graph on FIG. 7a, both signals were normalized to be between zero and 1. The area under each signal was integrated from zero to a max value going from zero to 40 micro seconds, the maximum extent of the flash lamp emission. This mimics an electric circuit that drives the flash lamp with a square pulse having a width varying from zero to 40 μsec. The output of these integrations represents the optical energy and thermal load of the flash lamp at each pulse width.

The energy outputs of the VIS-NIR 7201 and the UVC 7210 signals are shown in FIG. 7b. As can be seen, the total energy output of the UVC 7210 is delivered in the first 15 micro-seconds of the lamp drive signal, well before the total energy output of the VIS-NIR 7201 which it reaches at 40 micro-seconds. This is because the UVC pulse 7210 is shorter in time than the VIS-NIR 7201 pulse which is shown in FIG. 7a. This allows the driving signal to be shorter and still obtain the full energy from the UVC 7210 pulse. For the plasma flash lamp variation shown, the driving signal may be up to 25 micro-seconds shorter without significant loss of UVC energy.

Based on the above energy output profiles shown in FIG. 7b, driving such a flash lamp variation with a 9 μsec wide pulse would deliver a thermal load of approximately 60% of maximum, reducing thermal load by about 40%. This would deliver approximately 95% of the total energy available in the UVC.

A variation of a trigger circuit 5010 may be used to drive the flash lamp only long enough to get most of the UVC energy out of the lamp then turning off the driving pulse. The length of the driving pulse is proportional to the thermal load on the flash lamp. A shorter pulse will produce a smaller thermal load. Such a trigger circuit may be realized either by configuring the trigger circuit to trigger the pulse forming network associated with the flash lamp in a specific sequence, or by configuring the pulse forming network to respond to the trigger circuit 5010 in the desired way, or by a combination thereof. For solutions using COTS flash lamps, a programmable and/or configurable trigger circuit may be needed. In some variations, the flash lamp may itself be configurable for different driving pulses or pulse sequences.

Variations of such a pulse/illumination duration control solution may be used either instead of or in conjunction with heat sinking. If used in conjunction with heat sinking, the concept may allow for longer operating times for a lamp with a fixed heat sinking capacity. The concept may also allow for smaller flash lamp devices by eliminating or significantly reducing the size of the heat sink. Some variations may also include portable solutions that generate less heat and/or have smaller size/weight requirements. Furthermore, reducing the driving pulse of the flash lamp may also reduce battery consumption, allowing for longer operating times for battery-based devices.

Although discussed with respect to the UVC portion of a plasma flash lamp output, this technique is applicable for a broad range of flash lamp outputs and settings. Stated in more general terms, the concept relates to shortening a driving pulse for a flash lamp or similar pulsed illumination source in order to extract an output spectral range of interest that occurs closer to the start of illumination operation. By shortening the driving pulse in this way, a thermal load is reduced because the operating cycle of the device is shorter.

Scattered Light Control

In the latent fingerprint detection/illumination arrangements shown here, filtering may be realized with optical filter that uses reflective components rather than transmissive components. Reflective optical filtering is more efficient than transmissive filtering in the ultra-violet portion of the optical spectrum. All of the photons coming from the flash lamp or other illumination source must reflect off the optical components in order to be filtered. Any photons that get through the filter without reflecting off the optical components act as noise on the sample being illuminated. Photons that scatter off the filter housing or filter holders may find their way through the filter and hit the sample surface. Controlling the scattered light inside a filter housing disposed around the optical components may help to control the level of noise on the sample being illuminated.

By arranging optical baffles having specific shapes at particular locations within the optical beam path inside the filter housing, it is possible to control and at least partially absorb scattered light within the filter housing. In some variations, the baffles may also shape the illuminating beam so that it has the same aspect ratio as the FOV of a camera or imaging device photographing or otherwise imaging an illuminated target/sample.

In some variations described here, a latent fingerprint/contaminant detection system uses a flash lamp as the light source. In some variations, the flash lamp may have a parabolic or spherical or cylindrical or some other curved reflector behind the plasma to reflect the backward propagating photons towards the output. In some variations, the plasma has height, width, and depth on the order of a millimeter in each direction. In some variations, the parabolic/spherical/cylindrical/curved reflector has a focal length only a few times larger than the size of the plasma. This helps prevent the flash lamp from producing a truly collimated beam of light. In such variations, some of the photons from the plasma reflect off the parabolic/spherical/cylindrical/curved mirror and propagate out in somewhat of a beam. Some of the photons may miss the mirror and propagate out in somewhat of a spherical surface. Because of such photons that miss the mirror, along with the "beam" of light propagating out of the parabolic/spherical/cylindrical/curved reflector, there is a lot of light propagating from the flash lamp that does not resemble a beam at all.

Figure 8A:
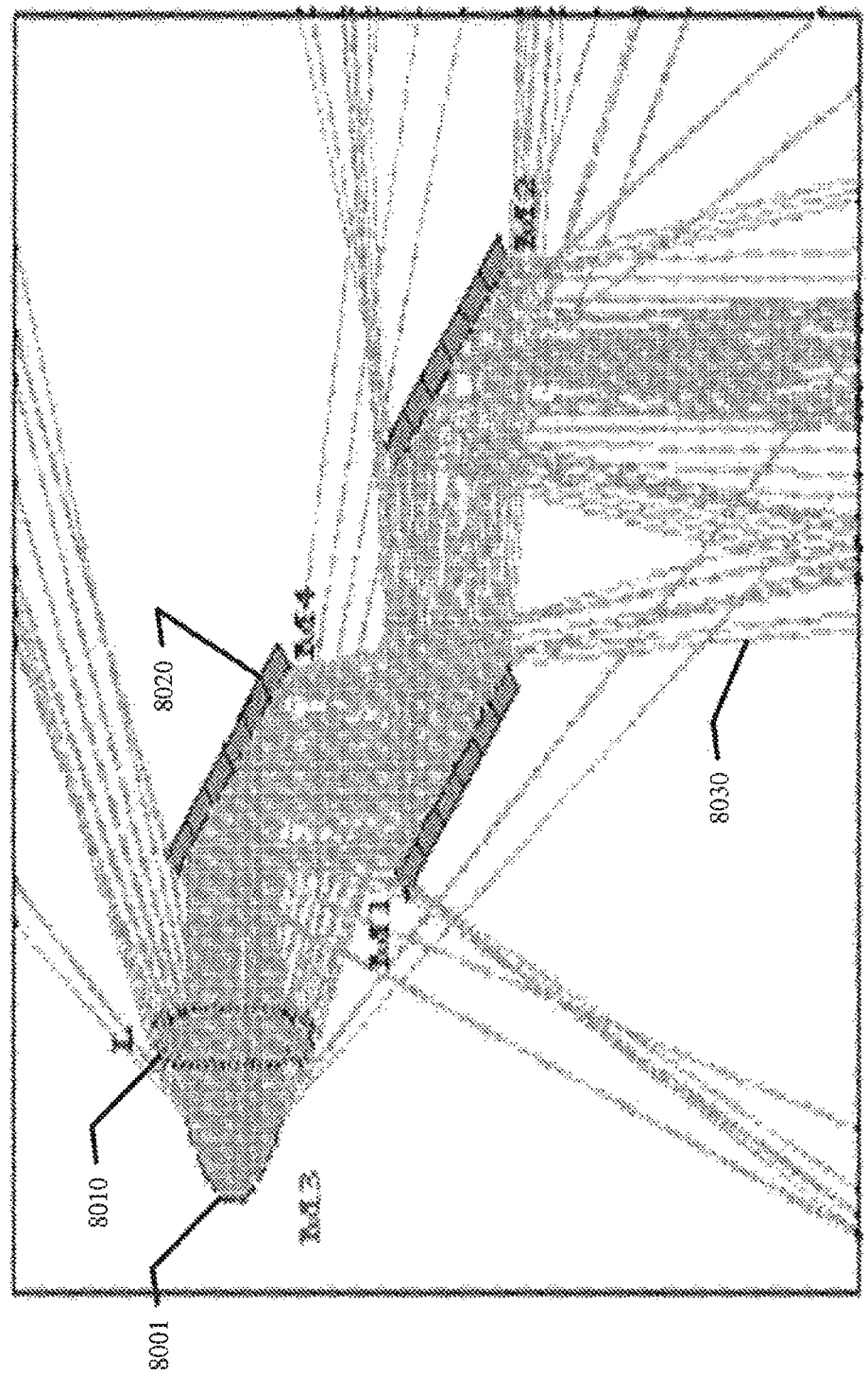
FIG. 8a depicts a variation of an illuminator for illuminating latent fingerprints as described herein.

In some variations, a positive lens may be placed in the path of the light coming out of the flash lamp. Such a variation is shown in FIG. 8*a*. As can be seen in the figure, some of the light coming off the flash lamp reflector 8001, acting like a beam, may come to a focus after passing through such a lens 8010. But the light that propagates along a spherical surface does not change much at all after passing through the lens. This light still diverges and will miss any optics, such as filter mirrors 8020, down range from the flash lamp, instead scattering off the optics/filter housing itself and creating noise 8030.

An optical system for latent fingerprint detection may include the above flash lamp and one or more reflective filters as depicted in FIG. 2*a*, 3*e*, and/or 6. Such variations of an optical system may be used as an illuminator for an imaging system. The mirrors in such a system filter the light to a state needed by the imaging equipment. Any light that misses the mirrors is not filtered and or partially filtered 8030 and may be considered as noise.

In some variations, such an illuminator may be contained within a closed housing. The housing walls may be configured to diffusely reflect and partially absorb any light that hits them. There are generally three classes of photons in such an illuminator, photons that: 1) hit the housing walls without encountering the mirrors (Unfiltered); 2) reflect off some or all of the mirrors and also hit the housing walls (Partially filtered); and 3) reflect off all the mirrors without hitting any other surfaces. (Fully filtered)

Figure 8B:
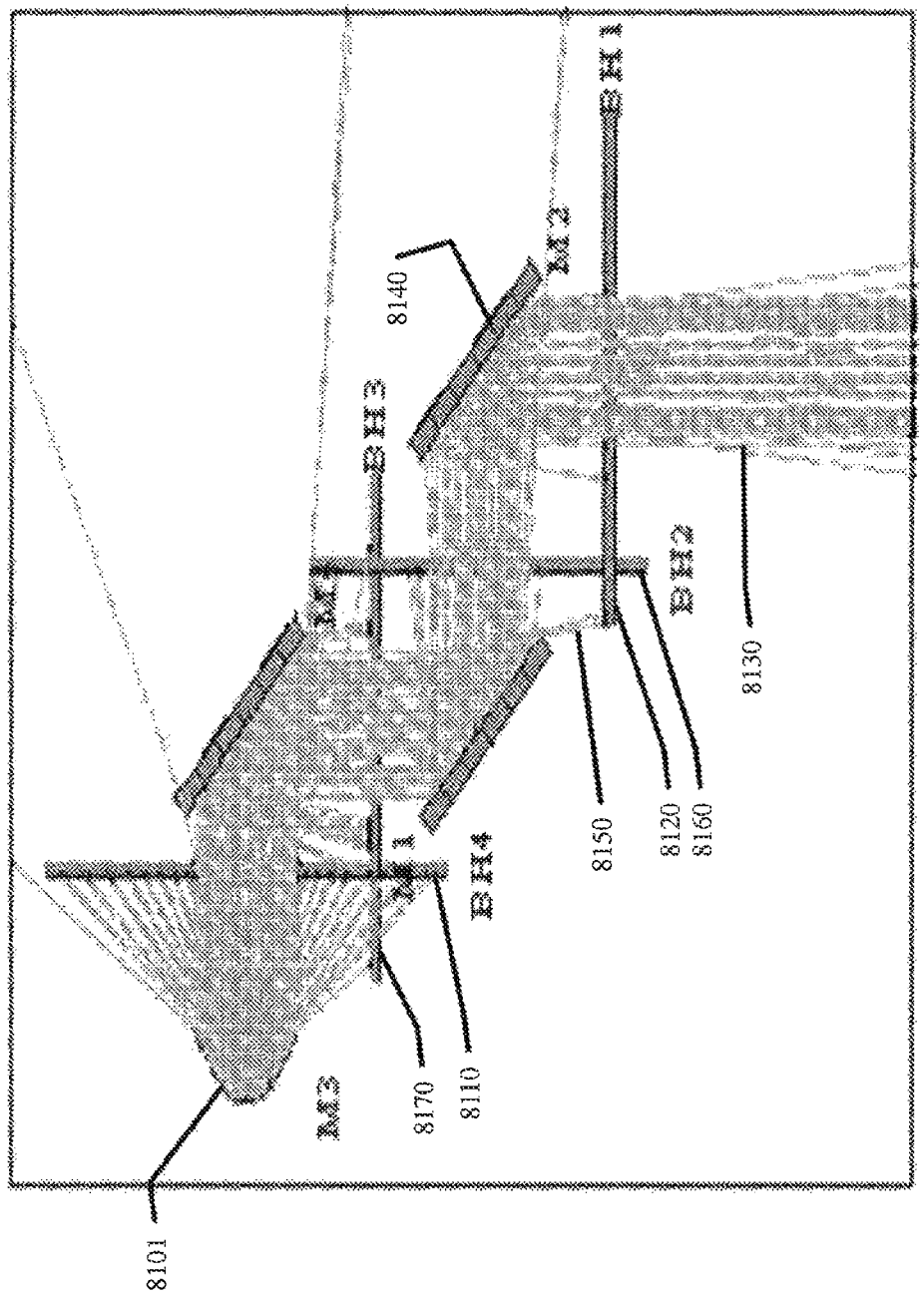
FIG. 8b depicts a variation of an illuminator for illuminating latent fingerprints as described herein.

In a preferred illuminator configuration, only the photons in class 3) should be allowed to reach the target. The other two classes of photons should be effectively blocked, or otherwise prevented from reaching the target. Allowing such unfiltered or partially filtered photons to reach the target will degrade the image. By adding baffles to the illuminator housing, the noise from divergent and scattered light may be reduced, thereby reducing the level of noise in the output of the illuminator. Such a variation is shown in FIG. 8*b*.

As can be seen in the figure, the baffles 8110, 8120, 8160, 8170 are sized and placed such that photons going straight to the target 8130 from the flash lamp 8101 are not obstructed but any other photons 8150 are blocked. The baffles after the flash lamp 8101 may be configured to allow only beam-shaped illumination from the flash lamp. Each optical filter element (in this case wavelength-specific mirrors) 8140 may also be equipped with a baffle 8120 that blocks divergent or scattered light 8150 from exiting the illuminator housing (not shown), thereby reducing or eliminating noise from the light directed to the illumination target 8130. In some variations, the holes in each baffle 8120, 8110, 8160, 8170 are sized so that photons passing directly from the flash lamp 8101, reflecting off the mirror(s) 8140, and falling within the defined illumination foot print on the target 8130 are allowed to pass through. Furthermore, a shape of the hole(s) in one or more baffles may affect the shape of the illumination on the target, with a round hole producing a round illumination and a rectangular hole producing a rectangular illumination. Also, such a technique also reduces the presence of a "hot spot" in the illumination on the target, making the illumination more uniform across the target and providing better detection results. In some variations, the baffle configuration shown in FIG. 8*b* may be combined with a negative lens to adjust a field of view (FOV) of the output illumination to a desired level.

Only exemplary embodiments of the present invention are shown and described in the present disclosure. It is to be understood that the present invention is capable of use in various other combinations and environments and is capable of changes or modifications within the scope of the inventive concept as expressed herein. Such variations are not to be regarded as departure from the spirit and scope of the invention, and all such modifications as would be obvious to one skilled in the art are intended to be included within the scope of the following claims:

What is claimed is:

1. A device for detecting a latent fingerprint on a substrate, the device comprising:
    an illumination source that emits illumination at a VUV (vacuum ultra-violet) wavelength range to illuminate an area on the substrate, wherein the illumination source is configured to cause the substrate to fluoresce providing visible spectrum contrast against the fingerprint which does not fluoresce; and
    a visible-spectrum imaging device that captures an image of the illuminated fingerprint contrasted against the fluorescing substrate;
    wherein the illumination source comprises a broad-spectrum light source and a waveband filtering device that filters all but the VUV illumination waveband out of the broad-spectrum generated by the broad-spectrum light source;
    wherein the waveband filtering device comprises a first mirror in optical communication with the broad-spectrum light source and a second mirror in optical communication with the first mirror;
    wherein the first and second mirrors both being wedge-shaped mirrors, each having a wedge angle that creates total internal reflection with respect to any light reflected from a back surface of the mirror; and
    wherein the first and second mirrors both being equipped with a VUV dielectric coating on a front reflecting surface such that each mirror reflects only the VUV illumination waveband from its front reflecting surface.

2. The device of claim 1, wherein the latent fingerprint remains untreated with any chemicals or contrast agents prior to illumination.

3. The device of claim 1, wherein the device further comprises a negative lens disposed between the broad-spectrum light source and the waveband filtering device.

4. The device of claim 1, wherein the optical elements are made of filter glass.

5. The device of claim 1, wherein the imaging device is a portable camera, the illumination source is mounted to the imaging device, and the device further comprises:
    an illumination source driver that drives the illumination source in response to an activation pulse;
    a power source that provides power to the illumination source driver and the illumination source; and
    a trigger circuit that controls activation pulse width and activation pulse rate of the illumination source.

6. The device of claim 1, wherein the illumination source comprises:
    a light-proof housing disposed around a light source and a waveband filtering device; and
    a first baffle disposed between the light source and the waveband filtering device, the first baffle being configured to exclude a portion of light emitted by light source, but not filtered by the waveband filtering device from the emitted illumination.

7. A device for detecting a latent fingerprint on a substrate, the device comprising:
    an illumination source that emits collimated illumination at a mid-wave or long-wave infra-red illumination to illuminate an area on the substrate, wherein the illumination source is configured to cause the substrate to fluoresce providing visible spectrum contrast against the fingerprint which does not fluoresce, wherein the latent fingerprint remains untreated with any chemicals or contrast agents prior to illumination; and
    an infra-red imaging device that captures an image of the illuminated fingerprint contrasted against the substrate;
    where the collimated infra-red beam source is capable of providing illumination to a target more than ten feet away from the illumination source for latent fingerprint detection; and where the imaging device is co-located with the infra-red beam source.

8. The device of claim 7, wherein the imaging device is a portable camera, the illumination source is mounted to the imaging device, and the device further comprises:
    an illumination source driver that drives the illumination source in response to an activation pulse;
    a power source that provides power to the illumination source driver and the illumination source; and
    a trigger circuit that controls activation pulse width and activation pulse rate of the illumination source.

9. The device of claim 7, wherein the illumination source comprises:
    a light-proof housing disposed around a light source and a waveband filtering device; and
    a first baffle disposed between the light source and the waveband filtering device, the first baffle being configured to exclude a portion of light emitted by light source, but not filtered by the waveband filtering device from the emitted illumination.

10. A device for detecting a latent fingerprint on a substrate, the device comprising:
    an illumination source that emits illumination at a VUV (vacuum ultra-violet) wavelength range to illuminate an area on the substrate, wherein the illumination source is configured to cause the substrate to fluoresce providing visible spectrum contrast against the fingerprint which does not fluoresce; and
    a visible-spectrum imaging device that captures an image of the illuminated fingerprint contrasted against the fluorescing substrate;
    where the illumination source includes a broad-spectrum light source and a waveband filtering device that filters all but the VUV illumination waveband out of the broadspectrum generated by the broad-spectrum light source;
    the waveband filtering device including a first optical element in optical communication with the broad-spectrum light source and a second optical element in optical communication with the first optical element;
    the first and second optical elements both being equipped with a VUV dielectric coating on a reflecting surface such that each optical element reflects only the VUV illumination waveband from the reflecting surface; and
    the first and second optical elements both being configured to remove light not reflected by the reflecting surface from the output illumination.

11. The device of claim 10, where the first and second optical elements are prisms.

12. The device of claim 10, wherein the latent fingerprint remains untreated with any chemicals or contrast agents prior to illumination.

13. The device of claim 10, wherein the device further comprises a negative lens disposed between the broad-spectrum light source and the waveband filtering device.

14. The device of claim 10, wherein the optical elements are made of glass.

15. The device of claim 10, wherein the imaging device is a portable camera, the illumination source is mounted to the imaging device, and the device further comprises:
- an illumination source driver that drives the illumination source in response to an activation pulse;
- a power source that provides power to the illumination source driver and the illumination source; and
- a trigger circuit that controls activation pulse width and activation pulse rate of the illumination source.

16. The device of claim 10, wherein the illumination source comprises:
- a light-proof housing disposed around a light source and a waveband filtering device; and
- a first baffle disposed between the light source and the waveband filtering device, the first baffle being configured to exclude a portion of light emitted by light source, but not filtered by the waveband filtering device from the emitted illumination.

\* \* \* \* \*